US005877011A

United States Patent [19]
Armentano et al.

[11] Patent Number: 5,877,011
[45] Date of Patent: Mar. 2, 1999

[54] CHIMERIC ADENOVIRAL VECTORS

[75] Inventors: Donna Armentano, Belmont; Richard J. Gregory, Westford; Alan E. Smith, Dover, all of Mass.

[73] Assignee: Genzyme Corporation, Framingham, Mass.

[21] Appl. No.: 752,760

[22] Filed: Nov. 20, 1996

[51] Int. Cl.[6] .................................................... C12N 15/86
[52] U.S. Cl. .................................... 435/320.1; 536/23.72
[58] Field of Search ............................... 435/69.1, 172.1, 435/172.3, 320.1, 235.1; 424/93.2, 93.6; 536/23.72, 23.1

[56] References Cited

U.S. PATENT DOCUMENTS 5,670,488   9/1997   Gregory et al. ........................... 514/44

OTHER PUBLICATIONS

Richard C. Boucher, TIG, vol. 12, No. 3, Mar. 1996, pp. 81–84.

Thomas Shenk, "Group C Adenovirsues as Vectors for Gene Therapy" in Viral Vectors, Kaplitt and Loewry, Eds., Academic Press, pp. 43–54.

Zabner et al., J. Clin. Invest., vol. 97, No. 6, Mar. 1996, pp. 1504–1511.

Orkin et al., "Report and Recommendations of the Panel to assess the NIH Investment in Research on Gene Therapy", Dec. 7, 1995.

T. Wickham, et al., "Penton Base Protein and Methods of Using Same", United States Patent No. 5,559,099, Filed Sep. 8, 1994, Issued Sep. 24, 1996.

McClelland, et al., International Patent Application No. PCT/US94/09172, filed Aug. 11, 1994, published Feb. 23, 1995 bearing Publication No. WO 95/05201.

A. Bailey, et al., "Phylogenetic Relationships Among Adenovirus Serotypes", *Virology*, 205, 1994, pp. 438–452.

R. Bernards, et al., "Oncogenicity by Adenovirus Is Not Determined by the Transforming Region Only", *Journal of Virology*, 50, 1984, pp. 847–853.

D. Curiel, et al., "Gene Therapy Approaches for Inherited and Acquired Lung Diseases", *American Jpurnal of Respiratory Cell and Molecular Biology*, 14, 1996, pp. 1–18.

C. Defer, et al., "Human Adenovirus–Host Cell Interactions: Comparative Study with Members of Subgroups B and C", *Journal of Virology*, 64, 1990, pp. 3661–3673.

F. Deryckere, et al., "Early Region 3 of Adenovirus Type 19 (Subgroup D) Encodes an HLA–Binding Protein Distinct from That of Subgroups B and C", *Journal of Virology*, 70, 1996, pp. 2832–2841.

J. Douglas, et al., "Targeted Gene Delivery by Tropism–Modified Adenoviral Vectors", *Nature Biotechnology*, 14, 1996, pp. 1574–1578.

B. Eiz, et al., "Immunological Adenovirus Variant Strains of Subgenus D: Comparison of the Hexon and Fiber Sequences", *Journal of Virology*, 213, 1995, pp. 313–320.

J. Gall, et al., "Adenovirus Type 5 and 7 Capsid Chimera: Fiber Replacement Alters Receptor Tropism without Affecting Primary Immune Neutralization Epitopes", *Journal of Virology*, 70, 1996, pp. 2116–2123.

Y. Gordon, et al., "Prolonged Recovery of Desiccated Adenoviral Serotypes 5, 8, and 19 from Plastic and Metal Surfaces In Vitro", *Ophthalmology*, 100, 1993, pp. 1835–1840.

L. Henry, et al., "Characterization of the Knob Domain of the Adenovirus Type 5 Fiber Protein Expressed in *Escherichia coli*", *Journal of Virology*, 68, 1994, pp. 5239–5246.

J. Hong, et al., "Domains Required for Assembly of Adenovirus Type 2 Fiber Trimers", *Journal of Virology*, 70, 1996, pp. 7071–7078.

A. Kajon, et al., "Sequence Analysis of the E3 Region and Fiber Gene of Human Adenovirus Genome Type 7h", *Virology*, 215, 1996, pp. 190–196.

N. Louis, et al., "Cell–Binding Domain of Adenovirus Serotype 2 Fiber", *Journal of Virology*, 68, 1994, pp. 4104–4106.

A. Mastrangeli, et al., "Sero–Switch" Adenovirus–Medicated in Vivo Gene Transfer: Circumvention of Anti–Adenovirus Humoral Immune Defenses Against Repeat Adenovirus Vector Administration by Changing the Adenovirus Serotype, *Human Gene Therapy*, 7, 1996, pp. 79–87.

P. Mathias, et al., "Multiple Adenovirus Serotypes Use α v Integrins for Infection", *Journal of Virology*, 68, 1994, pp. 6811–6814.

S. Michael, et al., "Addition of a Short Peptide Ligand to the Adenovirus Fiber Protein", *Gene Therapy*, 2, 1995, pp. 660–668.

N. Mittereder, et al., "Evaluation of the Concentration and Bioctivity of Adenovirus Vectors for Gene Therapy", *Journal of Virology*, 70, 1996, pp. 7498–7509.

P. Pring–Akerblom, et al., "Characterization of Adenovirus Subgenes D Fiber Genes", *Virology*, 206, 1995, pp. 564–571.

D. Rich, et al., "Development and Analysis of Recombinant Adenoviruses for Gene Therapy of Cystic Fibrosis", *Human Gene Therapy*, 4, 1993, pp. 461–476.

L. Roba, et al., "Adenoviral Ocular Isolates Demonstrate Serotype–Dependent Differences in In Vitro Infectivity Titers and Clinical Course", *Cornea*, 14, 1995, pp. 388–393.

(List continued on next page.)

*Primary Examiner*—David Guzo
*Attorney, Agent, or Firm*—Baker & Botts, L.L.P.

[57] ABSTRACT

A chimeric adenoviral vector is provided that comprises nucleotide sequence of a first adenovirus, wherein at least one gene of said first adenovirus encoding a protein that facilitates binding of said vector to a target mammalian cell, or internalization thereof within said cell, is replaced by the corresponding gene from a second adenovirus belonging to subgroup D, said vector further comprising a transgene operably linked to a eucaryotic promoter to allow for expression therefrom in a mammalian cell. Additionally, a method of delivering transgenes to target mammalian cells, particularly airway epithelial cells, is provided.

2 Claims, 4 Drawing Sheets

OTHER PUBLICATIONS

P. Roelvink, et al., "Comparative Analysis of Adenovirus Fiber–Cell Interaction: Adenovirus Type 2(Ad2) and Ad9 Utilize the Same Cellular Fiber Receptor but Use Different Binding Strategies for Attachment", *Journal of Virology,* 70, 1996, pp. 7614–7621.

S. Stevenson, et al., "Human Adenovirus Serotypes 3 and 5 Bind to Two Different Cellular Receptors via the Fiber Head Domain", *Journal of Virology,* 69, 1995, pp. 2850–2857.

M. Trousdale, et al., "Role of Adenovirus Type 5 Early Region 3 in the Pathogenesis of Ocular Disease and Cell Culture Infection", *Cornea,* 14, 1995, pp. 280–289.

T. Wickham, et al., "Adenovirus Targeted to Heparan–Containing Receptors Increases its Gene Delivery Efficiency to Multiple Cell Types", *Nature Biotechnology,* 14, 1996, pp. 1570–1573.

J. Wilson, "Adenovirsus as Gene–Delivery Vehicles", *New England Journal of Medicine,* 334, 1996, pp. 1185–1187.

J. Zabner, et al., "Repeat Administration of an Adenovirus Vector Encoding Cystic Fibrosis Transmembrane Conductance Regulator to the Nasal Epithelium of Patients with Cystic Fibrosis", *Journal of Clinical Investigations,* 97, 1996, pp. 1504–1511.

CHIMERIC ADENOVIRAL VECTORS

BACKGROUND OF THE INVENTION

The present invention relates to chimeric adenoviral vectors, that is, vectors comprising DNA from more than one serotype of adenovirus, that have enhanced capabilities to enter target mammalian cells in order to deliver therapeutically useful nucleotide sequences therein. Such a nucleotide sequence (which may be referred to as transgene) may comprise a gene not otherwise present in the target cell that codes for a therapeutically useful protein, or may represent, for example, an active copy of a gene that is already present in the target cell, but in a defective form.

One of the fundamental challenges now facing medical practicioners is that although the defective genes that are associated with numerous inherited diseases (or that represent disease risk factors including for various cancers) have been isolated and characterized, methods to correct the disease states themselves by providing patients with normal copies of such genes (the technique of gene therapy) are substantially lacking. Accordingly, the development of improved methods of intracellular delivery therefor is of great medical importance. Examples of diseases that it is hoped can be treated by gene therapy include inherited disorders such as cystic fibrosis, Gaucher's disease, Fabry's disease, and muscular dystrophy. Representative of acquired disorders that can be treated are: (1) for cancers—multiple myeloma, leukemias, melanomas, ovarian carcinoma and small cell lung cancer; (2) for cardiovascular conditions—progressive heart failure, restenosis, and hemophilias; and (3) for neurological conditions—traumatic brain injury.

Gene therapy requires successful transfection of target cells in a patient. Transfection may generally be defined as the process of introducing an expressible polynucleotide (for example a gene, a cDNA, or an mRNA patterned thereon) into a cell. Successful expression of the encoding polynucleotide leads to production in the cells of a normal protein and leads to correction of the disease state associated with the abnormal gene. Therapies based on providing such proteins directly to target cells (protein replacement therapy) have generally proved ineffective since, for example, the cell membrane presents a selectively permeable barrier to entry. Thus there is great interest in alternative methods to cause delivery of therapeutic proteins.

Cystic fibrosis, a common lethal genetic disorder, is a particular example of a disease that is a target for gene therapy. The disease is caused by the presence of one or more mutations in the gene that encodes a protein known as cystic fibrosis transmembrane conductance regulator ("CFTR"), and which regulates the movement of ions (and therefore fluid) across the cell membrane of epithelial cells, including lung epithelial cells. Abnormnal ion transport in airway cells leads to abnormal mucous secretion, inflammmation and infection, tisssue damage, and eventually death.

It is widely hoped that gene therapy will provide a long lasting and predictable form of therapy for certain disease states, and it is likely the only form of therapy suitable for many inhereted diseases. There remains however a critical need to develop vectors that faciliate entry of functional genes into cells, and whose activity in this regard provides in vivo delivery of genes that is sufficient for therapeutic effect.

Reported Developments

Most attempts to use viral vectors for gene therapy have relied on retrovirus-based vectors, chiefly because of their ability to integrate into the cellular genome. However, the disadvantages of retroviral vectors are becoming increasingly clear, including their tropism for dividing cells only, the possibility of insertional mutagenesis upon integration into the cell genome, decreased expression of the transgene over time, rapid inactivation by serum complement, and the possibility of generation of replication-competent retroviruses. See, for example, D. Jolly, et al., *Cancer Gene Therapy*, 1, 1994, pp. 51–64, and C. P. Hodgson, et al., *Bio Technology*, 13,1995, pp. 222–225.

Adenovirus is a nuclear DNA virus with a genome of about 36 kb, which has been well-characterized through studies in classical genetics and molecular biology (see, for example, M. S. Horwitz et al., "Adenoviridae and Their Replication," in *Virology* 2nd edition, B. N. Fields et al., eds., Raven Press, New York, 1990). In a simplified form, the genome is classified into early (known as E1–E4) and late (known as L1–L5) transcriptional units, referring to the generation of two temporal classes of viral proteins. The demarcation between these events is viral DNA replication.

Adenovirus-based vectors offer several unique advantages, including tropism for both dividing and non-dividing cells, minimal pathogenic potential, ability to replicate to high titer for preparation of vector stocks, and the potential to carry large therapeutic transgene inserts (see, for example, D. Jolly, *Cancer Gene Therapy* 1, 1994, pp. 51–64. The cloning capacity of present adenovirus vectors is about 8 kb, resulting typically from: (1) the deletion of certain regions of the virus genome dispensable for virus growth, for example, E3; and (2) deletions of regions, such as E1, whose function may be restored in trans, that is, from a packaging cell line such as the 293 cell, see F. L. Graham, *Gen. Virol.*, 36, pp. 59–72 (1977).

Genes that have been expressed to date using adenoviral vectors include p53 (Wills et al., *Human Gene Therapy*, 5, 1994, pp. 1079–188; dystrophin (Vincent et al., *Nature Genetics*, 5, 1993, pp. 130–134; erythropoietin (Descamps et al., *Human Gene Therapy*, 5, 1994, pp. 979–985; ornithine transcarbamylase (Perricaudet et al., *Human Gene Therapy*, 1, 1990, pp. 241–256; adenosine deaminase (Mitani et al., Human Gene Therapy, 5, 1994, pp. 941–948; interleukin-2 (Haddada et al., *Human Gene Therapy*, 4, 1993, pp. 703–711; and ∂1-antitrypsin Gaffe et al., *Nature Genetics* 1, 1992, pp. 372–378.

However, there is a critical medical need to further improve the ability of adenovirus-based vectors to successfully enter the cells of patients so that therapeuticaly useful genes can be expressed therein at therapeutically beneficial levels. The present invention addresses this goal.

SUMMARY OF THE INVENTION

The present invention provides for chimeric adenoviral vectors. In a representative aspect of the invention, the vectors further comprise nucleotide sequences coding for therapeutically useful proteins, and have enhanced tropism for airway epithelial cells.

Accordingly, there are provided chimeric adenoviral vectors comprising nucleotide sequence of a first adenovirus, wherein at least one gene of said first adenovirus encoding a protein that facilitates binding of said vector to a target mammalian cell, or internalization thereof within said cell, is replaced by the corresponding gene from a second adenovirus belonging to subgroup D, said vectors further comprising a transgene operably linked to a eucaryotic promoter to allow for expression therefrom in a mammalian cell.

In a preferred embodiment, said second adenovirus is selected from the group consisting of serotypes Ad 9, Ad 15, Ad 17, Ad 19, Ad 20, Ad 22, Ad 26, Ad 27, Ad 28, Ad 30, and Ad 39, and the replaced gene encodes fiber or penton base.

In a further preferred embodiment of the invention, there are provided chimeric adenoviral vectors comprising nucleotide sequence of a first adenovirus, wherein a portion of a gene thereof encoding a protein that facilitates binding of said vector to a target mammalian cell, or internalization thereof within said cell, is replaced by a portion of the corresponding gene from a second adenovirus belonging to subgroup D, said vectors further comprising a transgene operably linked to a eucaryotic promoter to allow for expression therefrom in a mammalian cell. In a representative aspect thereof, the replaced encoding sequence codes for a portion of Ad fiber or penton base.

Additional aspects of the invention include methods to provide therapeutic proteins in the airway epithelial cells of patients. According to this aspect of the invention, chimeric adenoviral vectors are used in which a nucleotide sequence of a first adenovirus is replaced by the corresponding nucleotide sequence of a second adenovirus. Preferably, the second adenovirus is a member of subgroup D, and the replaced nucleotide sequence encodes a polypeptide selected from the group consisting of Ad fiber, a fragment of Ad fiber, Ad penton base, and a fragment of Ad penton base.

A still further representative aspect of the invention involves providing a therapeutic protein in the airway epithelial cells of a patient by administering to said cells an adenoviral vector comprising elements of an Ad17 genome, and a transgene encoding said therapeutic protein that is operably linked to a eucaryotic promoter to allow for expression therefrom in a mammalian cell, under conditions whereby the transgene encoding said therapeutic protein is expressed, and therapeutic benefit is produced in said airway epithelial cells.

These and other aspects of the present invention are described in the Detailed Description of the Invention which follows directly.

Figure 1:
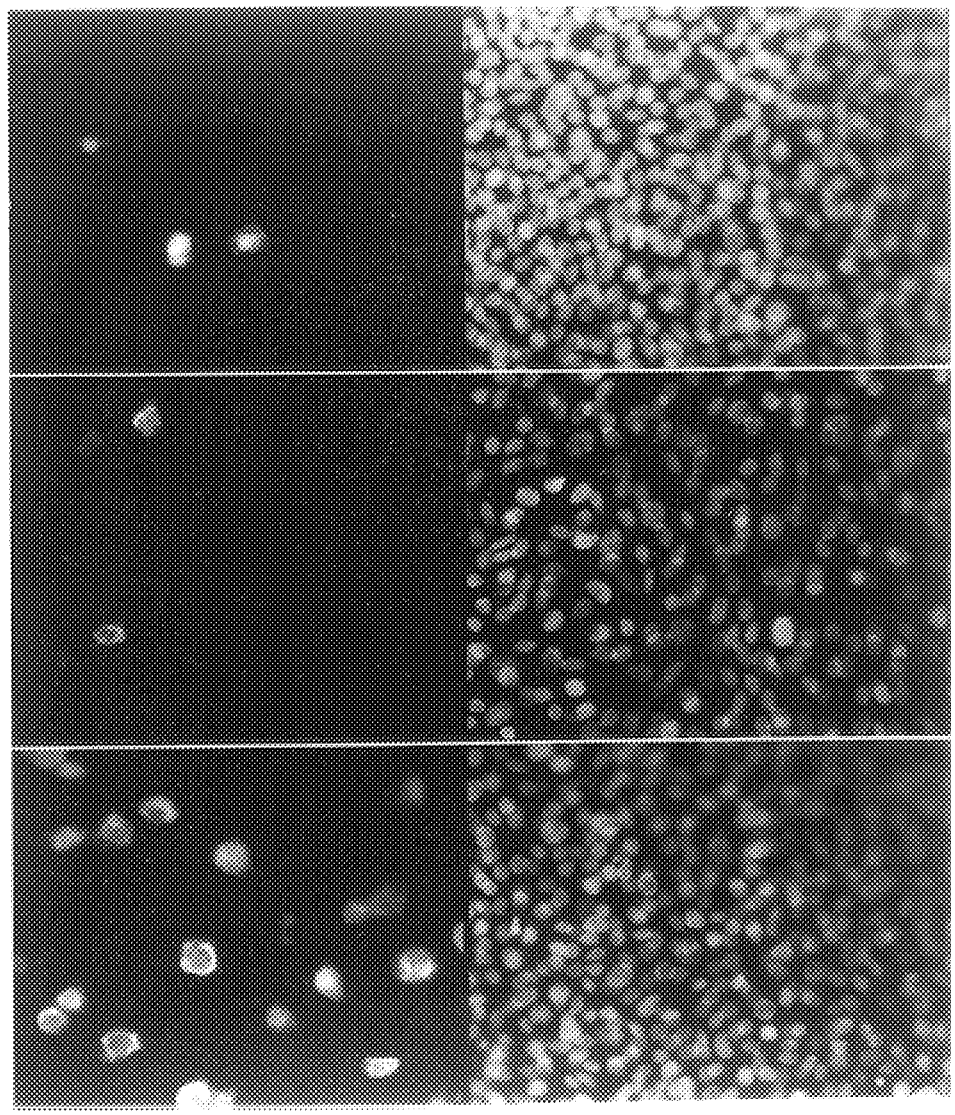
FIG. 1 (parts A–F) depicts infection of NHBE cells by Ad 2.

Provided in the Sequence Listing attached hereto are also:

SEQ ID NO: 1, the complete nucleotide sequence of Ad 17;

SEQ ID NO: 2, the complete encoding nucleotide sequence for Ad 17 fiber;

SEQ ID NO: 3, the complete encoding nucleotide sequence for Ad 17 penton base.

DETAILED DESCRIPTION OF THE INVENTION

A detailed discussion of adenovirus is found in M. S. Horwitz, "Adenoviridae and their Replication", and "Adenoviruses", Chapters 60 and 61, respectively, in Virology B. N. Fields et al., eds., 2nd edition, Raven Press, Ltd., New York, 1990, and reference therein is found to numerous aspects of adenovirus pathology, epidemiology, structure, replication, genetics and classification.

Briefly, the human adenoviruses (Ads) are divided into numerous serotypes (approximately 47, classified into 6 subgroups A, B, C, D, E and F), based upon properties including hemagglutination of red blood cells, oncogenicity, DNA base and protein amino acid compositions and homologies, and antigentic relationships (see for example M. S. Horwitz, above, at pages 1684–1685). Additional background information concerning Ad classification including for subgroup D can be found, for example, in F. Deryckere et al., *Journal of Virology*, 70, 1996, pp. 2832–2841; and A. Bailey et al., *Virology*, 205, 1994, pp. 438–452, and in other art-recognized references.

As recited by M. S. Horwitz, adenoviruses are nonenveloped, regular icosahedrons (having 20 triangular surfaces and 12 vertices) that are about 65–80 nm in diameter. A protein called "fiber" projects from each of these vertices. The fiber protein is itself generally composed of 3 identical polypeptide chains, although the length thereof varies between serotypes. The protein coat (capsid) is composed of 252 subunits (capsomeres), of which 240 are "hexons", and 12 are "pentons". Each of the pentons itself comprises a penton base, on the surface of the capsid, and a fiber protein projecting from the base. The Ad 2 penton base protein has been determined to be a 8×9 nm ring shaped complex composed of 5 identical protein subunits of 571 amino acids each. Additional background information may be found in U.S. Pat. No. 5,559,099 and references cited therein.

In general, it appears that adenovirus utilizes two cellular receptors to attach to, and then infect a target cell. It has been suggested that the fiber protein of an infecting adenovirus first attaches to a receptor, the identify of which is still unknown, and then penton base attaches to a further receptor, often a protein of the alpha integrin family. A review of this aspect of the art may be found, for example, in aforementioned U.S. Pat. No. 5,559,099. It has been determined that alpha-integrins often recognize short amino acid sequences on other cellular proteins for attachment purposes including the tripeptide sequence Arg-Gly-Asp (abbreviated RGD). An RGD sequence is found in penton base protein of adenovirus and is understood in the art to mediate attachment of Ad to alpha integrins.

The present invention involves the recognition that adenoviral vectors that are either based substantially upon the genome of Ad serotypes classified in subgroup D, or that contain certain Ad-protein encoding polynucleotide sequences of subgroup D adenovirus, are particularly effective at binding to, and internalizing within, human cells, such that therapeutic transgenes included in the adenoviral vector are efficiently expressed.

In a particularly important aspect of the invention, it has been determined that adenovirus serotypes within subgroup D are particularly effective to bind to and internalize within epithelial cells of the human respiratory system. This discovery is particularly surprising given that adenovirus serotypes of subgroup D are not clinically associated with human respiratory disease, and that, for example association with conjunctivitis is more typical. The recognition of this tropism is of particular importance for the treatment by gene therapy of recognized disease states of the lung such as cystic fibrosis or alpha 1-antitrypsin deficiency.

According to the practice of the invention, it is preferred that an adenovirus vector utilized to deliver a therapeutic transgene to the respiratory epithelium (including of the nasal airway, trachea, and bronchi and alveoli of the lung), or to other tissues of the body, be selected from the serotypes within subgroup D, as such classification is recognized in the art. Preferred serotypes include those selected from Ad 9, Ad 15, Ad 17, Ad 19, Ad 20, Ad 22, Ad 26, Ad 27, Ad 28, Ad 30, and Ad 39, although use of other, and potentially less effective, serotypes within subgroup D still provides a substantial improvement in the state of the art. A particularly effective adenoviral vector is that based upon the genome of Ad 17.

In connection with the design of adenoviral vectors based on the subgroup D viruses, reference may be made to the substantial body of literature on how such vectors may be designed, constructed and propagated, including for example, international patent publication WO 94/12649, wherein deletion of the E1 region, partial or complete deletion of the E4 region, and deletions within, for example, the E2 and E3 regions have been described. Of particular importance in the provision of such vectors is the existence of a complimenting cell line in which the vector can be maintained, for example, by analogy with the use of 293 cells to propagate Ad 2.

An important consideration in the generation of such cell lines is the provision by the host cells in trans of certain viral functions, that are desireably deleted from the vector, including, for example the E1a and E1b functions of adenovirus. That such cell lines can be readily generated according to the standard of the current art is evidenced by L. E. Babiss et al., *Journal of Virology*, 46, 1983, pp. 454–465. In this regard, the use of HER3 cells (human embryonic retinoblasts transformed by Ad 12), as a a complimenting cell line is of note.

Additionally, there is substantial evidence that any reported transforming properties of the E4 region of certain subgroup D serotypes do not extend to Ad serotypes whose use is preferred according to the practice of the present invention (see, for example, R. Javier et al., *Science*, 257, 1992, pp. 1267–1271). It is expected also that, for example, individual ORFs of the subgroup D E4 region, such as ORF1, could be deleted.

In an additional preferred aspect of the invention, the gene encoding a fiber, a penton base, or the genes for each, or for a subdomain of either or both, and derived from a serotype of subgroup D, is used in replacement for the corresponding encoding sequence from the starting Ad vector backbone. For the purposes of this example, "gene" means any nucleotide sequence, whether a gene, or a cDNA, and the like, that can be successfully used to express the protein product.

Examples

Example 1 Infection of NHBE cells by adenovirus serotypes of subgroup D

Normal human bronchial epithelial ("NHBE") cells were obtained from Clonetics (San Diego, Calif.), and plated on Costar (Cambridge, Mass.) Transwell-Clear polyester membranes that were pre-coated with human placental collagen. The wells were placed in a cluster plate and cells were fed every day for one week by changing the medium in both the well and the plate. After one week the media was removed from the wells to create an air-liquid interface, and the cells were then fed only by changing the medium in the cluster plate, every other day for one week. Cells were infected at an moi of 1 by adding virus (see below) to the transwell, followed by an incubation time of 1.5–2 hours. At the end of the incubation period, the medium was removed and the cells were gently rinsed with fresh medium. Thirty-six hours post-infection the cells were fixed with 1:1 acetone:methanol, permeablized with a solution of 0.05% Tween 20 in PBS, and stained with FITC labeled anti-hexon antibody (Chemicon, Temecula, Calif.) to visualize cells that had been productively infected (i.e. to visualize virus replication). Cells were also subjected to the DAPI staining procedure in order to visualize the total number of nuclei. The results could be readily determined upon simple inspection.

Wild type Ad serotypes within subgroup D that were tested included 9, 15, 17, 19, 20, 22, 26, 27, 28, 30, and 39 (all from the American Type Culture Collection, Rockville, Md.). An Ad 2 (obtained as DNA from BRL, Gaithersburg, Md., and used to transfect 293 cells in order to generate virus stock) was used as a control. Infection observed with all of the subgroup D serotypes was superior to that observed with Ad2, with the best results being achieved with Ad 9, Ad 17, Ad 20, Ad 22, and Ad 30.

Additionally, it was determined under similar circumstances that each of the above-mentioned serotypes of subgroup D was more effective in the NHBE cell assay than any other serotype tested than belongs to a subgroup other than D. In this regard, the following serotypes were tested: 31(subgroup A); 3(subgroup B); 7(subgroup B); 7a(subgroup B); 14(subgroup B); 4(subgroup E); and 41(subgroup F). In a further experiment, serotype 35 (subgroup A) may have performed as well as the least effective members of subgroup D that were tested.

Example 2 Infection of clinical isolate bronchial epithelial cells

Following generally the procedures of Example 1, human bronchial epithelial cells recovered from healthy human volunteers were infected with either Ad 2 (as above, Ad2 DNA was obtained from BRL, and this DNA was used to transfect 293 cells to generate virus) (FIG. 1), or Ad 17 (from ATCC) (FIG. 2), all at an moi of 50. Cells were left in contact with virus for 30 minutes , 3 hours, or 12 hours.

Figure 2:
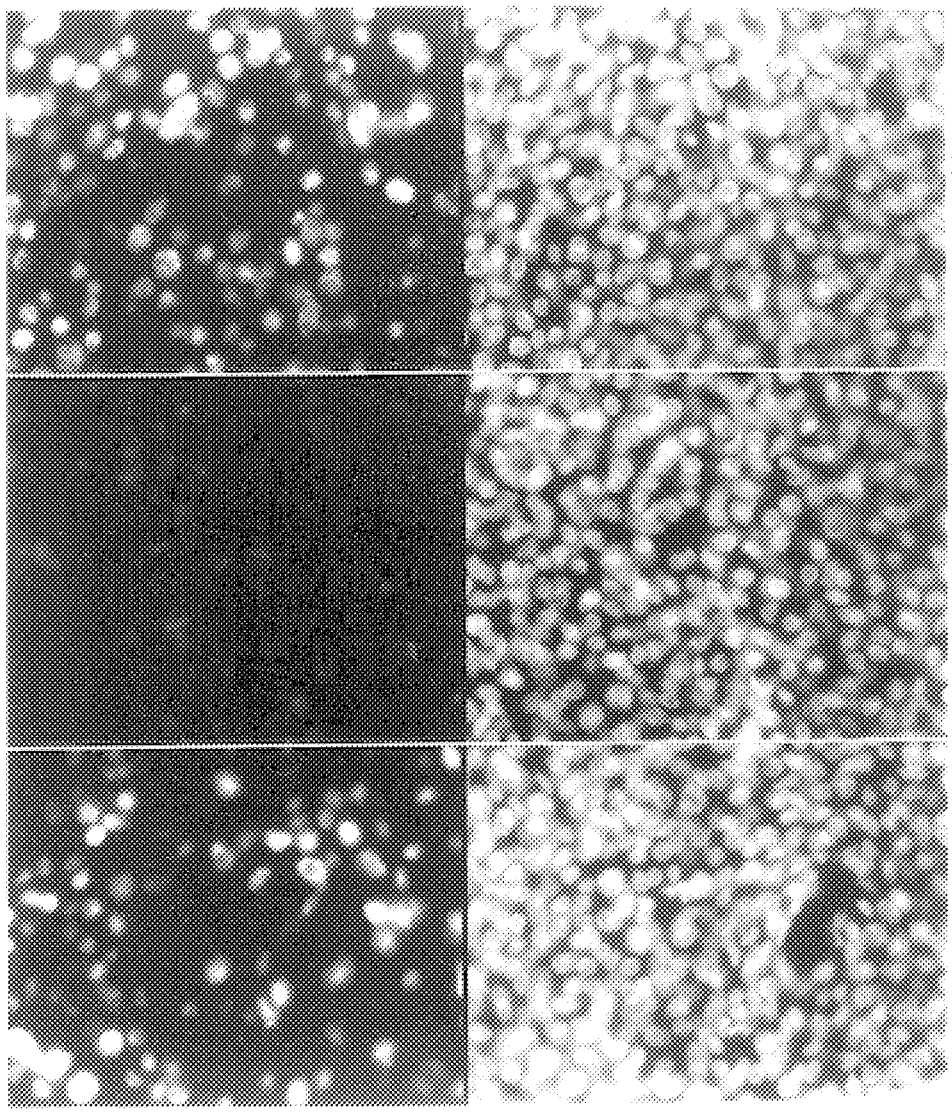
FIG. 2 (parts A–F) depicts infection of NHBE cells by Ad 17.

The increased tropism of Ad 17 for human bronchial epithelial cells, compared with Ad 2, is readily apparent upon inspection of FIGS. 1 and 2. In the Figures, the right hand columns (panels D, E, and F,. stained in blue) show total numbers of cells present (from DAPI staining as above), whereas the left hand columns (panels A, B, and C, stained in green) quantify adenovirus hexon protein present in the infected cells (from FITC-labeled anti-hexon antibody, as above). Panels A and D result from 30 minute incubation times, panels B and E result from 3 hour incubation times, and panels C and F result from 12 hour incubation times. As measured by the technique employed, infection of airway epithelia by Ad17 is at least 50 fold greater than by Ad 2 for the thirty minute incubation time.

Example 3 Binding of Ad 2 and Ad17 to human nasal polyp cell isolates 293 cells, a complementing cell line developed by Graham et al. (see *Gen. Virol.* , 36, 1977, pp. 59–72), were infected with either wild type Ad2 or wild type Ad17. Five hours post-infection the media was removed and replaced with methionine free media containing $S^{35}$ metabolic label (Amersham). After an additional six hours, fresh media was added and the labeling was allowed to proceed for a total of 18 hours, after which the $S^{35}$ media was removed and replaced with fresh media. Thirty hours post-infection the cells were harvested and lysed and the labeled Ad2 or Ad 17 viruses were purified by CsCl gradient centrifugation. The recovered viruses were then used in an assay to determine their relative binding efficiency on human nasal polyp cells.

Figure 3:
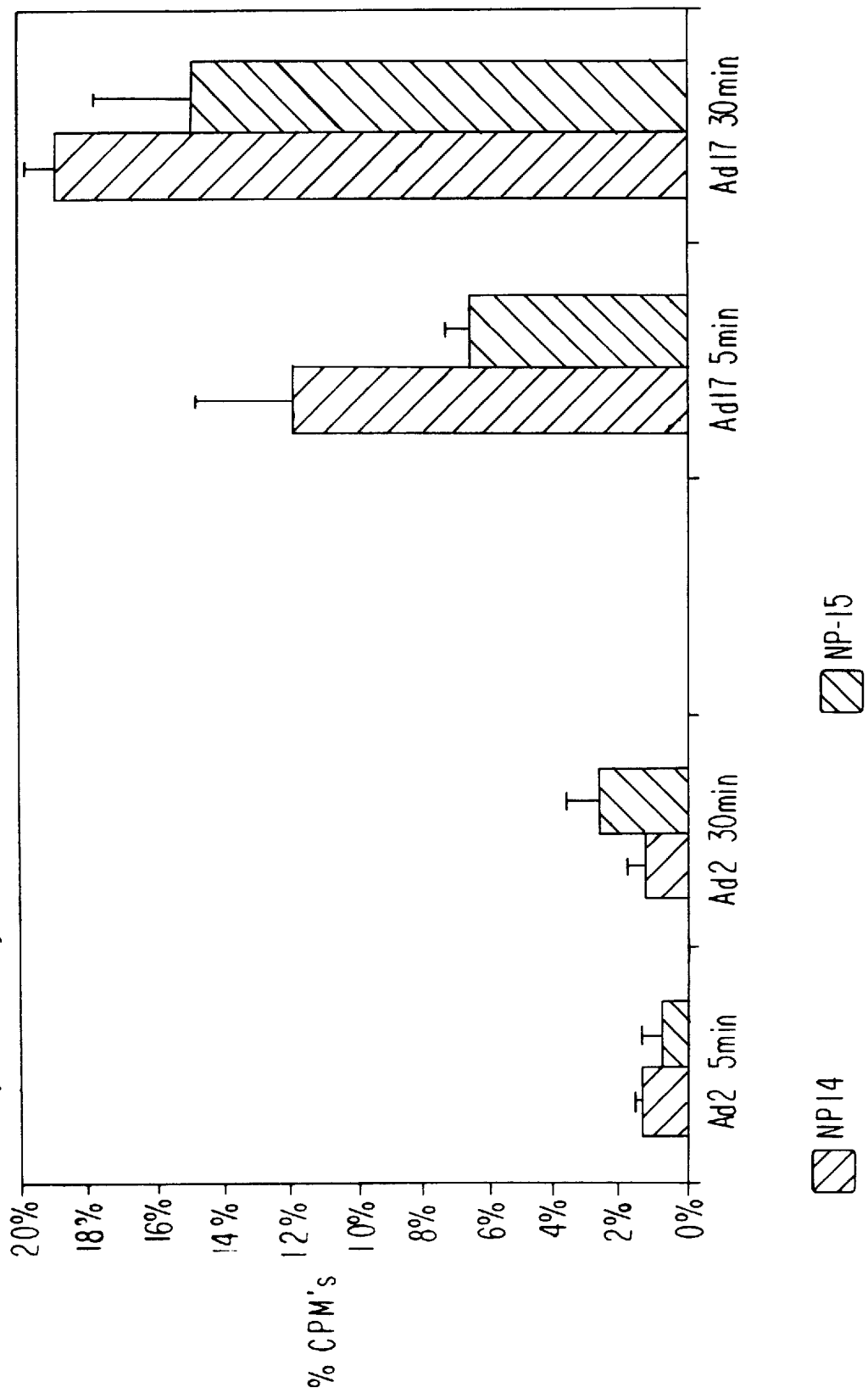
FIG. 3 plots the result of binding to human nasal polyp epithelial cell isolates by Ad 2 and Ad 17.

In order to perform the assay, ciliated human airway epitehlial cells were recovered from nasal polyps of healthy volunteers. The results from two such isolates, NP-14 and NP-15, are reported here (see FIG. 3). Radiolabeled virus was then incubated with the isolated cells in wells for specified times (5 or 30 minutes, see FIG. 3). The cells were then rinsed and measured for radioactivity. Binding as reported in FIG. 3 indicates the percent of input radioactivity that is cell associated. It was determined that for both cell isolate populations, using either 5 or 30 minute incubations, cell associated radioactivity was 10-fold enhanced if Ad 17 rather than Ad 2 was used.

Example 4 Fiber competition

A549 cells (a human lung carcinoma line, obtained from the American Type Culture Collection as ATCC CCL-185) were plated at $3 \times 10^4$ cells per well in 96-well dishes. Since the number of receptor sites for adenovirus fiber on the cell surface has been estimated to be approximately $10^5$ receptors per cell, the receptors in the plated cells were saturated, in this example, with 0.1 µg of purified full length Ad 2 fiber protein (obtained from Paul Freimuth, Brookhaven National Laboratory, Upton, N.Y.), which corresponds to approximately 100 molecules of fiber per receptor. Cells were incubated with Ad 2 fiber in PBS for two hours at 37° C.

The cells were subsequently infected at an moi of 1 (using either Ad2 provided as above, or wild type Ad 17) for one hour, after which the cells were rinsed, and fresh medium was added. Control cultures were incubated with PBS with no added protein for two hours and then subsequently infected as described above. Forty hours post-infection the cells were fixed with 1:1 acetone:methanol, permeablized with 0.05% Tween 20 in PBS and stained with FITC labeled anti- Ad2 hexon antibody, as described in Example 1. As determined by this assay, the number of cells infected (stained) with Ad2 was reduced by approximately 90% in cultures that were pre-incubated with Ad2 fiber as compared to control cultures. However, no effect on Ad17 infection was observed by the pre-incubation of A549 cells with full length Ad2 fiber.

Example 5 Use of Ad 2 fiber knob in a binding competition experiment with Ad 2

Further competition experiments were performed with Ad2 and Ad17 fiber knobs that had been expressed and purified from *E. coli*. DNA sequences encoding both protein fragments were designed so that the fiber knobs expressed therefrom would contain histidine tags in order to permit nickel-column purification. The yield of soluble fiber knob trimer, purified by the Ni-NTA method (Qiagen, Chatsworth, Calif.), was ~25µg/50 ml culture. A significant portion of the total knob protein expressed appeared to remain in a monomeric (and insoluble) form. The soluble trimeric material obtained was used for a preliminary competition experiment. Wild type Ad2 and Ad17 were used to infect A549 cells, or cells that had been pre-incubated with excess (about 100 molecules of trimer per receptor) Ad2 fiber knob or Ad17 fiber knob. The results indicated that Ad2 fiber knob, but not Ad17 knob, could block Ad 2 infection. Additionally, Ad 17 infection was not blocked by *E. coli*-expressed fiber knobs of either serotype, suggesting that the mechanism of Ad 2 and Ad 17 infections is different.

Example 6 Construction of the chimeric vector Ad2/βgal-2/fiber Ad17

The vector Ad2/βgal-2 was constructed as follows. A CMVβgal expression cassette was constructed in a pBR322-based plasmid that contained Ad2 nucleotides 1–10,680 from which nucleotides 357–3328 were deleted. The deleted sequences were replaced with (reading from 5' to 3'): a cytomegalovirus immediate early promoter (obtained from pRC/CMV, Invitrogen), lacZ gene encoding β-galactosidase with a nuclear localization signal, and an SV40 polyadenylation signal (nucleotides 2533–2729). The resulting plasmid was used to generate Ad2/βgal-2 by recombination with Ad2E4ORF6 (D. Armentano et al., Human Gene Therapy, 6, 1995, pp 1343–1353).

Figure 4:
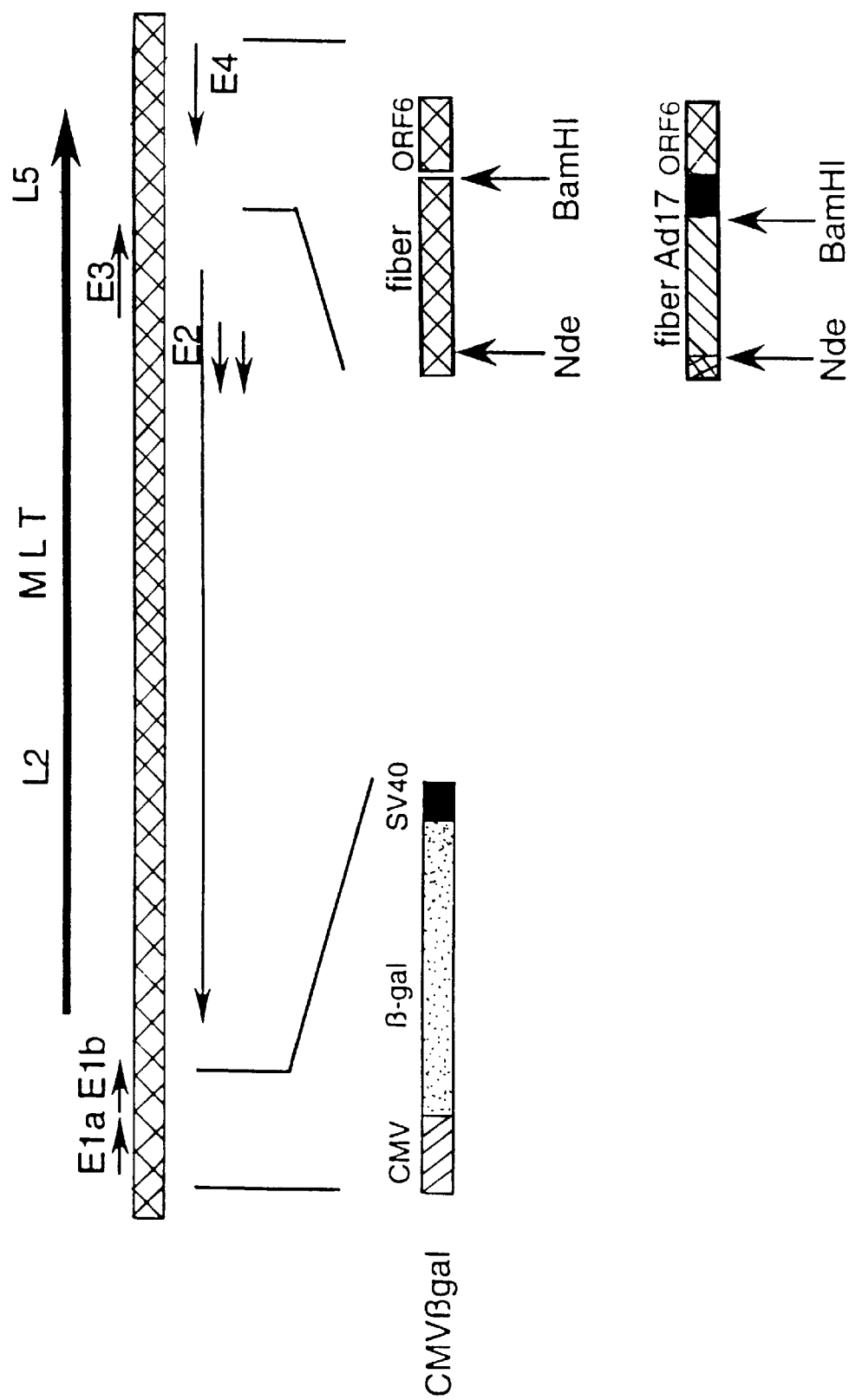
FIG. 4 is a map of the vector Ad2/βgal-2/fiber Ad17.

A chimeric Ad2/βgal-2/fiber Ad17 viral vector (FIG. 4) was then constructed as follows. pAdORF6 (D. Armentano et al., *Human Gene Therapy* 6, 1995, pp 1343–1353 was cut with Nde and BamHI to remove Ad2 fiber coding and polyadenylation signal sequences (nucleotides 20624–32815). An NdeI-BamHI fragment containing Ad17 fiber coding sequence (nucleotides 30835–32035) was generated by PCR and ligated along with an SV40 polyadenylation signal into NdeI-BamHI cut pAdORF6 to generate pAdORF6fiber17. This plasmid was cut with Pacd and then ligated to PacI-cut Ad2/βgal-2 DNA to generate Ad2/βgal-2fiber 17. A therapeutic transgene may be substituted in this construct for the reporter gene.

A similar construct can be prepared using a DNA sequence that encodes Ad 17 penton base instead of Ad 17 fiber. Alternatively only a subregion of the penton base of Ad 2 need be subject to replacement, such as by inserting into the vector a nucleotide encoding sequence corresponding to any amino acid subsequence of Ad 17 penton base amino acids 283–348 in replacement for any subsequence of Ad 2 penton base amino acids 290–403. Preferably, the replaced sequence of Ad 2 and the inserted sequence of Ad 17 includes the RGD domain of each. Use of nucleotide sequence corresponding to penton base amino acid sequence for other subgroup D serotypes is also within the practice of the invention.

We claim:

1. A chimeric adenoviral vector, wherein the genome of said vector comprises the nucleotide sequence of a first adenovirus having one or more E4 open reading frames deleted while retaining sufficient E4 sequences to promote virus replication in vitro, and further comprising a transgene operably linked to a eucaryotic promoter to allow for expression therefrom in a mammalian cell, wherein the nucleotide sequence encoding fiber protein of said first adenovirus is replaced by a corresponding nucleotide sequence encoding fiber protein from a second adenovirus and wherein said first adenovirus is Ad 2, and said second adenovirus is Ad 17.

2. A chimeric adenoviral vector, wherein the genome of said vector comprises the nucleotide sequence of a first adenovirus having one or more E4 open reading frames deleted while retaining sufficient E4 sequences to promote virus replication in vitro, and further comprising a transgene operably linked to a eucaryotic promoter to allow for expression therefrom in a mammalian cell, wherein the nucleotide sequence encoding fiber protein of said first adenovirus is replaced by a corresponding nucleotide sequence encoding fiber protein from a second adenovirus and wherein said first adenovirus is Ad 5, and said second adenovirus is Ad 17.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 35081 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CATCATCAAT    AATATACCCC    ACAAAGTAAA    CAAAAGTTAA    TATGCAAATG    AGGTTTTAAA        60
```

-continued

| | | | | | | |
|---|---|---|---|---|---|---|
| TTTAGGGCGG | GGCTACTGCT | GATTGGCCGA | GAAACGTTGA | TGCAAATGAC | GTCACGACGC | 120 |
| ACGGCTAACG | GTCGCCGCGG | AGGCGTGWCT | AGCCCGGAAG | CAAGTCGCGG | GGCTGATGAC | 180 |
| GTATAAAAAA | GCGGACTTTA | AACCCGGAAA | CGGCCGATTT | TCCCGCGGCC | ACGCCCGGAT | 240 |
| ATGAGGTAAT | TCTGGGCGGA | TGCAAGTGAA | ATTAGGTCAT | TTTGGCGCGA | AAACTGAATG | 300 |
| AGGAAGTGAA | AAGTGAAAAA | TACCGGTCCC | GCCCAGGGCG | GAATATTTAC | CGAGGGCCGA | 360 |
| GAGACTTTGA | CCGATTACGT | GTGGGTTTCG | ATTGCGGTGT | TTTTTCGCGA | ATTTCCGCGT | 420 |
| CCGTGTCAAA | GTCCGTGTT | TATGTCACAG | ATCAGCTGAT | CCACAGGGTA | TTTAAACCAG | 480 |
| TCGAGCCCGT | CAAGAGGCCA | CTCTTGAGTG | CCAGCGAGTA | GAGATTTCTC | TGAGCTCCGC | 540 |
| TCCCAGAGTG | TGAGAAAAAT | GAGACACCTG | CGCCTCCTGC | CTGGAACTGT | GCCCTTGGAC | 600 |
| ATGGCCGCAT | TATTGCTGGA | TGACTTTGTG | AGTACAGTAT | GGAGGATGA | ACTGCAACCA | 660 |
| ACTCCGTTCG | AGCTGGGACC | CACACTTCAG | GACCTCTATG | ATTTGGAGGT | AGATGCCCAG | 720 |
| GAGGACGACC | CGAACGAAGA | TGCTGTGAAT | TTAATATTTC | CAGAATCTCT | GATTCTTCAG | 780 |
| GCTGACATAG | CCAGCGAAGC | TCTACCTACT | CCACTTCATA | CTCCAACTCT | GTCACCCATA | 840 |
| CCTGAATTGG | AAGAGGAGGA | CGAGTTAGAC | CTCCGGTGTT | ATGAGGAAGG | TTTTCCTCCC | 900 |
| AGCGATTCAG | AGGACGAACA | GGGTGAGCAG | AGCATGGCTC | TAATCTCAGA | CTATGCTTGT | 960 |
| GTGGTTGTGG | AAGAGCATTT | TGTGTTGGAC | AATCCTGAGG | TGCCCGGGCA | AGGCTGTAAA | 1020 |
| TCCTGCCAGT | ACCACCGGGA | TAAGACCGGA | GACACGAACG | CCTCCTGTGC | TCTGTGTTAC | 1080 |
| ATGAAAAAGA | ACTTCAGCTT | TATTTACAGT | AAGTGGAGTG | AATGTGAGAG | AGGCTGAGTG | 1140 |
| CTTAAGACAT | AACTGGGTGA | TGCTTCAACA | GCTGTGCTAA | GTGTGGTTTA | TTTTGTTTCT | 1200 |
| AGGTCCGGTG | TCAGAGGATG | GTCATCACCC | TCAGAAGAAG | ACCACCCGTG | TCCCCCTGAT | 1260 |
| CTGTCAGGCG | AAACGCCCCT | GCAAGTGCAC | AGACCCACCC | CAGTCAGACC | CAGTGGCGAG | 1320 |
| AGGCGAGCAG | CTGTTGAAAA | AATTGAGGAC | TTGTTACATG | ACATGGGTGG | GGATGAACCT | 1380 |
| TTGGACCTGA | GCTTGAAACG | TCCCAGGAAA | CTAGGCGCAG | CTGCGCTTAG | TCATGTGTAA | 1440 |
| ATAAAGTTGT | ACAATAAAAA | TTATATGTGA | CGCATGCAAG | GTGTGGTTTA | TGACTCATGG | 1500 |
| GCGGGGCTTA | GTTCTATATA | AGTGGCAACA | CCTGGGCACT | GGAGCACAGA | CCTTCAGGGA | 1560 |
| GTTCCTGATG | GATGTGTGGA | CTATCCTTGC | AGACTTTAGC | AAGACACGCC | GGCTTGTAGA | 1620 |
| GGATAGTTCA | GACGGGTGCT | CCGGGTTCTG | GAGACACTGG | TTTGGAACTC | CTCTATCTCG | 1680 |
| CCTGGTGTAC | ACAGTTAAAA | AGGATTATAA | CGAGGAATTT | GAAAATCTTT | TTGCTGATTG | 1740 |
| CTCTGGCCTG | CTAGATTCTC | TGAATCTCGG | CCACCAGTCC | CTTTTCCAGG | AAAGGGTACT | 1800 |
| CCACAGCCTT | GATTTTTCCA | GCCCAGGGCG | CACTACAGCC | GGGGTTGCTT | TTGTGGTTTT | 1860 |
| TCTGGTTGAC | AAATGGAGCC | AGAACACCCA | ACTGAGCAGG | GGCTACATTC | TGGACTTCGC | 1920 |
| AGCCATGCAC | CTGTGGAGGG | CATGGGTCAG | GCAGCGGGGA | CAGAGAATCT | TGAACTACTG | 1980 |
| GCTTCTACAG | CCAGCAGCTC | CGGGTCTTCT | TCGTCTACAC | AGACAAACAT | CCATGTTGGA | 2040 |
| GGAAGAAATG | AGGCAGGCCA | TGGACGAGAA | CCCGAGGAGC | GGTCTGGACC | CTCCGTCGGA | 2100 |
| AGAGGAGTTG | GATTGAATCA | GGTATCCAGC | CTGTACCCAG | AGCTTAGCAA | GGTGCTGACA | 2160 |
| TCCATGGCCA | GGGGAGTGAA | GAGGGAGAGG | AGCGATGGGG | GCAATACCGG | GATGATGACC | 2220 |
| GAGCTGACGG | CCAGTCTGAT | GAATCGCAAG | CGCCCAGAGC | GCCTTACCTG | GTACGAGCTA | 2280 |
| CAGCAGGAGT | GCAGGGATGA | GTTGGGCCTG | ATGCAGGATA | AATATGGCCT | GGAGCAGATA | 2340 |
| AAAACCCATT | GGTTGAACCC | AGATGAGGAT | TGGGAGGAGG | CTATTAAGAA | GTATGCCAAG | 2400 |
| ATAGCCCTGC | GCCCAGATTG | CAAGTACATA | GTGACCAAGA | CCGTGAATAT | CAGACATCCT | 2460 |

```
GCTACATCTC  GGGGAACGGG  GCAGAGGTGG  TCATTGATAC  CCTGGACAAG  GCCGCCTTTA  2520
GGTGTTGCAT  GATGGGAATG  AGAGCCGGAG  TGATGAATAT  GAATTCCATG  ATCTTTATGA  2580
ACATGAAGTT  CAATGGAGAG  AAGTTTAATG  GGGTGCTGTT  CATGGCCAAC  AGCCACATGA  2640
CCCTGCATGG  CTGCGACTTT  TTCGGCTTTA  ACAATATGTG  CGCAGAGGTC  TGGGGCGCTT  2700
CCAAGATCAG  GGGATGTAAG  TTTTATGGCT  GCTGGATGGG  CGTGGTCGGA  AGACCCAAGA  2760
GCGAGATGTC  TGTGAAGCAG  TGTGTGTTTG  AGAAATGCTA  CCTGGGAGTC  TCTACCGAGG  2820
GCAATGCTAG  AGTGAGGCAC  TGCTCTTCCC  TGGAGACGGG  CTGCTTCTGC  CTGGTGAAGG  2880
GCACAGCCTC  TCTGAAGCAT  AATATGGTGA  AGGGCTGCAC  GGATGAGCGC  ATGTACAACA  2940
TGCTGACTGC  GACTCGGGGG  TCTGTCATAT  CCTGAAGAAC  ATCCATGTGA  CCTCCCACCC  3000
CAGAAAGAAG  TGGCCAGTGT  TTGAGAATAA  CATGCTGATC  AAGTGCCACA  TGCACCTGGG  3060
CGCCAGAAGG  GGCACCTTCC  AGCCGTACCA  GTGCAACTTT  AGCCAGACCA  AGCTGCTGTT  3120
GGAGAACGAT  GCCTTCTCCA  GGGTGAACCT  GAACGGCATC  TTTGACATGG  ATGTCTCGGT  3180
GTACAAGATC  CTGAGATACG  ATGAGACCAA  GTCCAGGGTG  CGCGCTTGCG  AGTGCGGGGG  3240
CAGACACACC  AGGATCCAGC  CAGTGGCCCT  GGATGTGACC  GAGGAGCTGA  GACCAGACCA  3300
CCTGGTGATG  GCCTGTACCG  GGACCGAGTT  CAGCTCCAGT  GGGGAGGACA  CAGATTAGAG  3360
GTAGGTTTGA  GTAGTGGGCG  TGGCTAAGGT  GACTATAAAG  GCGGGTGTCT  TACGAGGGTC  3420
TTTTTGCTTT  TCTGCAGACA  TCATGAACGG  GACCGGCGGG  GCCTTCGAAG  GGGGGCTTTT  3480
TAGCCCTTAT  TTGACAACCC  GCCTGCCAGG  ATGGGCCGGA  GTTCGTCAGA  ATGTGATGGG  3540
ATCGACGGTG  GACGGGCGCC  CAGTGCTTCC  AGCAAATTCC  TCGACCATGA  CCTACGCGAC  3600
CGTGGGGAAC  TCGTCGCTTG  ACAGCACCGC  CGCAGCCGCG  GCAGCCGCAG  CCGCCATGAC  3660
AGCGACGAGA  CTGGCCTCGA  GCTACATGCC  CAGCAGCAGC  AGTAGCCCCT  CTGTGCCCAG  3720
TTCCATCATC  GCCGAGGAGA  ACTGCTGGCC  CTGCTGGCCG  AGCTGGAAGC  CCTGAGCCGC  3780
CAGCTGGCCG  CCCTGACCCA  GCAGGTGTCC  GAGCTCCGCG  AACAGCAGCA  GCAAAATAAA  3840
TGATTCAATA  AACACATATT  CTGATTCAAA  CAGCAAAGCA  TCTTTATTAT  TTATTTTTTC  3900
GCGCGCGGTA  GGCCCTGGTC  CACCTCTCCC  GATCATTGAG  AGTGCGGTGG  ATTTTTTCCA  3960
AGACCCGGTA  GAGGTGGGAT  TGGATGTTGA  GGTACATGGG  CATGAGCCCG  TCCCGGGGGT  4020
GGAGGTAGCA  CCACTGCATG  GCCTCGTGCT  CGGWTCGTGT  TGTAGATGAT  CCAGTCATAG  4080
CAGGGGCGCG  GGCGTGGTGC  TGGATGATGT  CCTTGAGGAG  GAGACTGATG  CCACGGGGA   4140
GCCCCTTGGT  GTAGGTGTTG  GCAAAGCGGT  TGAGCTGGGA  GGGATGCATG  CGGGGGGAGA  4200
TGATGTGCAG  TTTGGCCTGG  ATCTTGAGGT  TGGCGATGTT  GCCACCCAGA  TCCCGCCGGG  4260
GGTTCATGTT  GTGCAGGACC  ACCAGGACGG  TGTAGCCCGT  GCACTTGGGG  AACTTATCAT  4320
GCAACTTGGA  AGGGAATGCG  TGGAAGAATT  TGGAGACGCC  CTTGTGCCCG  CCCAGGTTTT  4380
CCATGCACTC  ATCCATGATG  ATGGCGATGG  GCCCGTGGGC  TGCGGCTTTG  GCAAAGACGT  4440
TTCTGGGGTC  AGAGACATCA  TAATTATGCT  CCTGGGTGAG  ATCATCATAA  GACATTTTAA  4500
TGAATTTTGG  GCGGAGGGTG  CCAGATTGGG  GGACGATGGT  TTCCCTCGGG  CCCCGGGGCG  4560
AAGTTCCCCT  CGCAGATCTG  CATCTCCCAG  GCTTTCATCT  CGGAGGGGGG  GATCATGTCC  4620
ACCTGCGGGG  CGATGAAAAA  AACGGTTTCC  GGGGCGGGGG  TGATGAGCTG  CGAGGAGAGC  4680
AGGTTTCTCA  ACAGCTGGGA  CTTGCCGCAC  CCGGTCGGGC  CGTAGATGAC  CCCGATGACG  4740
GGTTGCAGGT  GGTAGTTCAA  GGACATGCAG  CTGCCGTCGT  CCCGGAGGAG  GGGGGCCACC  4800
TCGTTGAGCA  TGTCTCTAAC  TTGGAGGTTT  TCCCGGACGA  GCTCGCCGAG  GAGGCGGTCC  4860
```

```
CCGCCCAGCG AGAGGAGCTC TTGCAGGGAA GCAAAGTTTT TCAGGGGCTT GAGTCCGTCG      4920
GCCATGGGCA TCTTGGCGAG GGTCTGCGAG AGGAGTTCGA GACGTCCCAG AGCTCGGTGA      4980
CGTGCTCTAC GGCATCTCGA TCCAGCAGAC TTCCTCGTTT CGGGGGTTGG GACGACTGCG      5040
ACTGTAGGGC ACGAGACGAT GGGCGTCCAG CGCGGCCAGC GTCATGTCCT TCCAGGGTCT      5100
CAGGGTCCGC GTGAGGGTGG TCTCCGTCAC GGTGAAGGGG TGGGCCCCTG GCTGGGCGCT      5160
TGCAAGGGTG CGCTTGAGAC TCATCCTGCT GGTGCTGAAA CGGGCACGGT CTTCGCCCTG      5220
CGCGTCGGCG AGATAGCAGT TGACCATGAG CTCGTAGTTG AGGGCCTCGG CGGCGTGGCC      5280
CTTGGCGCGG AGCTTGCCCT TGGAAGAGCG TCCGCAGGCG GGACAGAGGA GGGATTGCAG      5340
GGCGTAGAGC TTGGGCGCAA GAAAGACCGA CTCGGGAGCA AAAGCGTCCG CTCCGCAGTG      5400
GGCGCAGACG GTCTCGCACT CGACGAGCCA GGTGAGCTCG GCTGCTCGG GGTCAAAAAC      5460
CAGTTTTCCC CCGTTCTTTT TGATGCGCTT CTTACCTCGC GTCTCCATGA GTCTGTGTCC      5520
GCGCTCGGTG ACAAACAGGC TGTCGGTGTC CCCGTAGACG GACTTGATTG CCTGTCCTG      5580
CAGGGGCGTC CCGCGGTCCT CCTCGTAGAG AAACTCGGAC CACTCTGAGA CAAAGGCGCG      5640
CGTCCACGCC AAGACAAAGG AGGCCACGTG CGAGGGGTAG CGGTCGTTGT CCACCAGGGG      5700
GTCCACCTTT TCCACCGTGT GCAGACACAT GTCCCCTTCC TCCGCATCCA AGAAGGTGAT      5760
TGGCTTGTAG GTGTAGGCCA CGTGACCAGG GGTCCCCGAC GGGGGGGTAT AAAAGGGGC      5820
GGGTCTGTGC TCGTCCTCAC TCTCTTCCGC GTCGCTGTCC ACGAGCGCCA GCTGTTGGGG      5880
TAGGTATTCC CTCTCGAGAG CGGGCATGAC CTCGGCACTC AGGTTGTCAG TTTCTAGAAA      5940
CGAGGAGGAT TTGATGTTGG CTTGCCCTGC CGCAATGCTT TTTAGGAGAC TTTCATCCAT      6000
CTGGTCAGAA AAGACTATTT TTTTATTGTC AAGCTTGGTG GCAAAGGAGC CATAGAGGGC      6060
GTTGGAGAGA AGCTTGGCGA TGGATCTCAT GGTCTGATTT TTGTCACGGT CGGCGCGCTC      6120
CTTGGCCGCG ATGTTGAGCT GGACATATTC GCGCGCGACA CACTTCCATT CGGGAAAGAC      6180
GGTGGTGCGC TCGTCGGGCA CGATCCTGAC GCGCCAGCCG CGGTTATGCA GGGTGACCAG      6240
GTCCACGCTG GTGGCCACCT CGCCGCGCAG GGGCTCGTTA GTCCAGCAGA GTCTGCCGCC      6300
CTTGCGCGAG CAGAACGGGG GCAGCACATC AAGCAGATGC TCGTCAGGGG GGTCCGCATC      6360
GATGGTGAAG ATGCCGGGAC AGAGTTTCTT GTCAAAATAG TCTATTTTTG AGGATGCATC      6420
ATCCAAGGCC ATCTGCCACT CGCGGGCGGC CATTGCTCGC TCGTAGGGGT TGAGGGGCGG      6480
ACCCCACGGC ATGGGATGCG TGAGGGCGGA GGCGTACATG CCGCAAATGT CGTAAACATA      6540
GATGGGCTCC GAGAAGATGC CGATGTTGGT GGGATAACAG CGCCCCCGC GGATGCTGGC      6600
GCGCACGTAT TCATACAACT CGTGCGAGGG GCCAAGAAGG CCGGGGCCGA AATTGGTGCG      6660
CTGGGGCTGC TCGGCGCGGA AAACAATCTG GCGAAAGATG GCGTGCGAGT TGGAGGAGAT      6720
GGTGGGCCGT TGGAAGATGT TAAAGTGGGC GTGGGCAAG CGGACCGAGT CGCGGATGAA      6780
GTGCGCGTAG GAGTCTTGCA GCTTGGCGAC GAACTCGGCG GTGACGAGAA CGTCCATGGC      6840
GCAGTAGTCC AGCGTTTCGC GGATGATGTC ATAACCCGCC TCTCCTTTCT TCTCCCACAG      6900
CTCGCGGTTG AGGGCGTATT CCTCGTCATC CTTCCAGTAC TCCCGGAGCG GAATCCTCG      6960
ATCGTCCGCA CGGTAAGAGC CCAGCATGTA GAAATGGTTC ACGGCCTTGT AGGGACAGCA      7020
GCCCTTCTCC ACGGGAGGG CGTAAGCTTG TGCGGCCTTG CGGAGCGAGG TGTGCGTCAG      7080
GGCGAAGGTG TCCCTGACCA TGACTTTCAA GAACTGGTAC TTGAAATCCG AGTCGTCGCA      7140
GCCGCCGTGC TCCCATAGCT CGAAATCGGT GCGCTTCTTC GAGAGGGGT TAGGCAGAGC      7200
GAAAGTGACG TCATTGAAGA GAATCTTGCC TGCTCGCGGC ATGAAATTGC GGGTGATGCG      7260
```

```
GAAAGGGCCC GGGACGGAGG CTCGGTTGTT GATGACCTGG GCGGCGAGGA CGATCTCGTC  7320
GAAGCCGTTG ATGTTGTGCC CGACGATGTA GAGTTCCATG AATCGCGGGC GGCCTTTGAT  7380
GTGCGGCAGC TTTTTGAGCT CCTCGTAGGT GAGGTCCTCG GGCATTGCA GGCCGTGCTG   7440
CTCGAGCGCC CATTCCTGGA GATGTGGGTT GGCTTGCATG AAGGAAGCCC AGAGCTCGCG  7500
GGCCATGAGG GTCTGGAGCT CGTCGCGAAA GAGGCGGAAC TGCTGGCCCA CGGCCATCTT  7560
TTCGGGTGTG ACGCAGTAGA AGGTGAGGGG GTCCCGCTCC CAGCGATCCC AGCGTAAGCG  7620
CGCGGCTAGA TCGCGAGCAA GGGCGACCAG CTCTGGGTCC CCCGAGAATT TCATGACCAG  7680
CATGAAGGGG ACGAGCTGCT TGCCGAAGGA CCCCATCCAG GTGTAGGTTT CTACATCGTA  7740
GGTGACAAAG AGCCGCTCCG TGCGAGGATG AGAGCCGATT GGGAAGAACT GGATTTCCTG  7800
CCACCAGTTG GACGAGTGGC TGTTGATGTG ATGAAAGTAG AAATCCCGCC GGCGAACCGA  7860
GCACTCGTGC TGATGCTTGT AAAAGCGTCC GCAGTACTCG CAGCGCTGCA CGGGCTGTAC  7920
CTCATCCACG AGATACACAG CGCGTCCCTT GAGGAGGAAC TTCAGGAGTG GCGGCCCTGG  7980
CTGGTGGTTT TCATGTTCGC CTGCGTGGGA CTCACCCTGG GGCTCCTCGA GGACGGAGAG  8040
GCTGACGAGC CCGCGCGGGA GCCAGGTCCA GATCTCGGCG CGGCGGGGGC GGAGAGCGAA  8100
GACGAGGGCG CGCAGTTGGG AGCTGTCCAT GGTGTCGCGG AGATCCAGGT CCGGGGGCAG  8160
GGTTCTGAGG TTGACCTCGT AGAGGCGGGT GAGGGCGTGC TTGAGATGCA GATGGTACTT  8220
GATTTCTACG GGTGAGTTGG TGGCCGTGTC CACGCATTGC ATGAGCCCGT AGCTGCGCGG  8280
GGCCACGACC GTGCCGCGGT GCGCTTTTAG AAGCGGTGTC GCGGACGCGC TCCCGGCGGC  8340
AGCGGCGGTT CCGGCCCCGC GGGCAGGGGC GGCAGAGGCA CGTCGGCGTG GCGCTCGGGC  8400
AGGTCCCGGT GTTGCGCCCT GAGAGCGCTG GCGTGCGCGA CGACGCGGCG GTTGACATCC  8460
TGGATCTGCC GCCTCTGCGT GAAGACCACT GGCCCCGTGA CTTTGAACCT GAAAGACAGT  8520
TCAACAGAAT CAATCTCGGC GTCATTGACG GCGGGCTGAC GCAGGATCTC TTGCACGTCG  8580
CCCGAGTTGT CCTGGTAGGC GATCTCGGAC ATGAACTGCT CGATCTCCTC CTCCTGGAGA  8640
TCGCCGCGAC CCGCGCGCTC CACGGTGGCG GCGAGGTCAT TCGAGATGCG ACCCATGAGC  8700
TGCGAGAAGG CGCCCAGGCC GCTCTCGTTC CAGACGCGGC TGTAGACCAC GTCCCCGTCG  8760
GCGTCGCGCG CGCGCATGAC CACCTGCGCG AGGTTGAGCT CCACGTGCCG CGCGAAGACG  8820
GCGTAGTTGC GCAGGCGCTG GAAGAGGTAG TTGAGGGTGG TGGCGATGTG CTCGGTGACG  8880
AAGAAGTACA TGATCCAGCG GCGCAGGGGC ATCTCGCTGA TGTCGCCGAT GGCCTCCAGC  8940
CTTTCCATGG CCTCGTAGAA ATCCACGGCG AAGTTGAAAA ACTGGGCGTT GCGGGCCGAG  9000
ACCGTGAGCT CGTCTTCCAG GAGCCTGATG AGCTCGGCGA TGGTGGCGCG CACCTCGCGC  9060
TCGAAATCCC CGGGGGCCTC GTCCTCTTCC TCTTCTTCCA TGACAACCTC TTCTATTTCT  9120
TCCTCTGGGG GCGGTGGTGG TGGCGGGGCC CGACGACGAC GGCGACGCAC CGGGAGACGG  9180
TCGACGAAGC GCTCGATCAT CTCCCCGCGG CGGCGACGCA TGGTTTCGGT GACGGCGCGA  9240
CCCCGTTCGC GAGGACGCAG CGTGAAGACG CCGCCGGTCA TCTCCCGGTA ATGGGGCGGG  9300
TCCCCGTTGG GCAGCGAGAG GGCGCTGACG ATGCATCTTA TCAATTGCGG TGTAGGGGAC  9360
GTGAGCGCGT CGAGATCGAC CGGATCGGAG AATCTTTCGA GGAAAGCGTC TAGCCAATCG  9420
CAGTCGCAAG GTAAGCTCAA ACACGTAGCA GCCCTGTGGA CGCTGTTAGA ATTGCGGTTG  9480
CTAATGATGT AATTGAAGTA GGCGTTTTTG AGGCGGCGGA TGGTGGCGAG GAGGACCAGG  9540
TCCTTGGGTC CCGCTTGCTG GATGCGGAGC CGCTCGGCCA TGCCCCAGGC CTGGCCCTGA  9600
CACCGGCTTA GGTTCTTGTA GTAGTCATGC ATGAGCCTCT CGATGTCATC ACTGGCGGAG  9660
```

```
GCGGAGTCTT CCATGCGGGT GACCCCGACG CCCCTGAGCG GCTGCACGAG CGCCAGGTCG    9720
GCGACGACGC GCTCGGCGAG GATGGCCTGT TGCACGCGGG TGAGGGTGTC CTGGAAGTCG    9780
TCCATGTCGA CGAAGCGGTG GTAGGCCCCT GTGTTGATGG TGTAAGTGCA GTTGGCCATG    9840
AGCGACCAGT TGACGGTCTG CAGGCCGGGC TGCACGACCT CGGAGTACCT GAGCCGCGAG    9900
AAGGCGCGCG AGTCGAAGAC GTAGTCGTTG CAGGTGCGCA CAAGGTACTG GTATCCGACT    9960
AGGAAGTGCG GCGGCGGCTG GCGGTAGAGC GGCCAGCGCT GGGTGGCCGG CGCGCCCGGG   10020
GCCAGGTCCT CGAGCATGAG GCGGTGGTAG CCGTAGAGGT AGCGGGACAT CCAGGTGATG   10080
CCGGCAGCGG TGGTGGAGGC GCGCGGGAAC TCGCGGACGC GGTTCCAGAT GTTGCGCAGC   10140
GGCAGGAAAT AGTCCATGGT CGGCACGGTC TGGCCGGTGA GACGCGCGCA GTCATTGACG   10200
CTCTAGAGGC AAAAACGAAA GCGGTTGAGC GGGCTCTTCC TCCGTAGCCT GGCGGAACGC   10260
AAACGGGTTA GGCCGCGCGT GTACCCCGGT TCGAGTCCCC TCGAATCAGG CTGGAGCCGC   10320
GACTAACGTG GTATTGGCAC TCCCGTCTCG ACCCGAGCCC GATAGCCGCC AGGATACGCG   10380
GGAAGAGCCC TTTTTGCCGG CCGARGGGAG TCGCTAGACT TGAAAGCGGC CGAAAACCCC   10440
GCCGGGTAGT GGCTCGCGCC CGTAGTCTGG AGAAGCATCG CCAGGGTTGA GTCGCGGCAG   10500
AACCCGGTTC GCGGACGGCC GCGGCGAGCG GGACTTGGTC ACCCCGCCGA TTTAAAGACC   10560
CACAGCCAGC CGACTTCTCC AGTTACGGGA GCGAGCCCCC TTTTTTCTTT TTGCCAGATG   10620
CATCCCGTCC TGCGCCAAAT GCGTCCCACC CCCCGGCGA CCACCGCGAC CGCGGCCGTA   10680
GCAGGCGCCG GCGCTAGCCA GCCACAGCCA CAGACAGAGA TGGACTTGGA AGAGGGCGAA   10740
GGGCTGGCGA GACTGGGGGC GCCTTCCCCG GAGCGACACC CCCGCGTGCA GCTGCAGAAG   10800
GACGTGCGCC CGGCGTACGT GCCTGCGCAA AACCTGTTCA GGGACCGCAG CGGGGAGGAG   10860
CCCGAGGAGA TGCGCGACTG CCGGTTTCGG GCGGGCAGGG AGCTGCGCGA GGGCCTGGAC   10920
CGCCAGCGCG TGCTGCGCGA CGAGGATTTC GAGCCGAACG AGCAGACGGG GATCAGCCCC   10980
GCGCGCGCGC ACGTGGCGGC GGCCAACCTG GTGACGGCCT ACGAGCAGAC GGTGAAGCAG   11040
GAGCGCAACT TCCAAAAGAG TTTCAACAAC CATGTGCGCA CCCTGATCGC GCGCGAGGAG   11100
GTGGCCCTGG GCCTGATGCA CCTGTGGGAC CTGGCGGAGG CCATCGTGCA GAACCCGGAC   11160
AGCAAGCCTC TGACGGCGCA GCTGTTCCTG GTGGTACAGC ACAGCAGGGA CAACGAGGCG   11220
TTCAGGGAGG CGCTGCTAAA CATCGCCGAG CCCGAGGGTC GCTGGCTGCT GGAGCTGATC   11280
AACATCTTGC AGAGCATCGT AGTTCAGGAG CGCAGCCTGA GCTTGGCCGA GAAGGTGGCG   11340
GCAATCAACT ACTCGGGCTT AGCCTGGGCA AGTTTTACGC GCGCAAGATT TACAAGACGC   11400
CGTACGTGCC CATAGACAAG GAGGTGAAGA TAGACAGCTT TTACATGCGC ATGGCGCTCA   11460
AGGTGCTGAC GCTGAGCGAC GACCTGGGCG TGTACCGCAA CGACCGCATC CACAAGGCCG   11520
TGAGCGCGAG CCGGCGGCGC GAGCTGAGCG ACCGCGAGCT GATGCTGAGC CTGCGCCGGG   11580
CGCTGGTAGG GGGCGCCGCC GGCGGCGAGG AGTCYTACTT CGACATGGGG GCGGACCTGC   11640
ATTGGCAGCC GAGCCGGCGC GCCTTGGAGG CCGCCTACGG TCCAGAGGAC TTGGATGAGG   11700
AAGAGGAAGA GGAGGAGGAT GCACCCGCTG CGGGGTACTG ACGCCTCCGT GATGTGTTTT   11760
TAGATGCAGC AAGCCCCGGA CCCCGCCATA AGGGCGGCGC TGCAAAGCCA GCCGTCCGGT   11820
CTAGCATCGG ACGACTGGGA GGCTGCGATG CAACGCATCA TGGCCCTGAC GACCCGCAAC   11880
CCCGAGTCCT TTAGACAACA GCCGCAGGCC AACAGACTCT CGGCCATTCT GGAGGCGGTG   11940
GTCCCTTCTC GGACCAACCC CACGCACGAG AAGGTGCTGG CGATCGTGAA CGCGCTGGCG   12000
GAGAACAAGG CCATCCGTCC CGACGAGGCC GGGCTAGTGT ACAACGCCCT GCTGGAGCGC   12060
```

```
GTAGGCCGCT ACAACAGCAC AAACGTGCAG TCCAACCTGG ACCGGCTGGT GACGGACGTG 12120
CGCGAAGCCG TGGCGCAGCG CGAGCGGTTC AAGAACGAGG GCCTGGGCTC GCTGGTGGCG 12180
CTGAACGCCT TCCTGGCGAC GCAGCCGGCG AACGTGCCGC GCGGGCAGGA TGATTACACC 12240
AACTTTATCA GCGCGCTGCG GCTGATGGTG ACCGAGGTGC CCCAGAGCGA GGTGTACCAG 12300
TCGGGCCCGG ACTACTTTTT CCAAACTAGC AGACAGGGCC TGCAAACGGT GAACCTGAGC 12360
CAGGCTTTCA AGAACCTGCG CGGGCTGTGG GGCGTGCAGG CGCCCGGGGC GACCGGTCGA 12420
CGGTGAGCAG CTTGCTGACG CCCAACTCGC GGCTGCTGCT GCTGCTGATC GCGCCCTTCA 12480
CCGACAGTGG CAGCGTAAAC CGCAACTCGT ACCTGGGTCA CCTGCTAACG CTGTACCGCG 12540
AGGCCATAGG CCAGGCGCAG GTGGACGAGC AGACCTTCCA GGAGATCACT AGCGTGAGCC 12600
GCGCGCTGGG GCAGAACGAC ACCGACAGTC TGAGGGCCAC CCTGAACTTC TTGCTGACCA 12660
ATAGACAGCA GAAGATCCCG GCGCAGTACG CGCTGTCGGC CGAGGAGGAG CGCATCCTGA 12720
GATATGTGCA GCAGAGCGTA GGGCTTTTCC TGATGCAGGA GGGGGCCACT CCCAGCGCCG 12780
CGCTGGACAT GACCGCGCGC AACATGGAAC CTAGCATGTA CGCCGCCAAC CGGCCGTTTA 12840
TCAATAAGCT AATGGACTAC CTGCATCGCG CGGCGTCCAT GAACTCGGAC TACTTTACCA 12900
ATGCCATTTT GAACCCGCAC TGGCTTCCGC CGCCGGGGTT CTATACGGGC GAGTACGACA 12960
TGCCCGACCC CAACGACGGG TTTTTGTGGG ACGACGTGGA CAGCGCGGTG TTTTCACCGA 13020
CCTTGCAAAA GCGCCAGGAG GCGGTGCGCA CGCCCGCGAG CGAGGGCGCG GTGGGTCGGA 13080
GCCCCTTTCC TAGCTTAGGG AGTTTGCATA GCTTGCCGGG CTCTGTGAAC AGCGGCAGGG 13140
TGAGCCGGCC GCGCTTGCWG CGAGGACGAG TACCTGAACG ACTCGCTGCT GCAGCCGCCG 13200
CGGGTCAAGA ACGCCATGGC CAATAACGGG ATAGAGAGTC TGGTGGACAA ACTGAACCGC 13260
TGGAAGACCT ACGCTCAGGA CCATAGGGAG CCTGCGCCCG CGCCGCGGCG ACAGCGCCAC 13320
GACCGGCAGC GGGGCCTGGT GTGGACGAC GAGGACTCGG CCGACGATAG CAGCGTGTTG 13380
GACTTGGGCG GGAGCGGTGG GGTCAACCCG ATATCGCGCA TCCTGCAGCC CAAACTGGGG 13440
CGACGGATGT TTTGAATGCA AAATAAAACT CACCAAGGCC ATAGCGTGCG TTCTCTTCCT 13500
TGTTAGAGAT GAGGCGTGCG GTGGTGTCTT CCTCTCCTCC TCCCTCGTAC GAGAGCGTGA 13560
TGGCGCAGGC GACCCTGGAG GTTCCGTTTG TGCCTCCGCG GTATATGGCT CCTACGAGG 13620
GCAGAAACAG CATTCGTTAC TCGGAGCTGG CTCCGTTGTA CGACACCACT CGCGTGTACT 13680
TGGTGGACAA CAAGTCGGCG GACATCGCTT CCCTGAACTA TCAAAACGAC CACAGCAACT 13740
TCCTGACCAC GGTGGTGCAG AACAACGATT TCACCCCCGC CGAGGCTAGC ACGCAGACGA 13800
TAAATTTTGA CGAGCGGTCG CGGTGGGGCG GTGATCTGAA GACCATTCTG CACACCAACA 13860
TGCCCAATGT GAACGAGTAC ATGTTCACCA GCAAGTTTAA GGCGCGGGTG ATGGTGGCTA 13920
GAAAACACCC ACAGGGGTA GAAGCAACAG ATTTAAGCAA GGATATCTTA GAGTATGAGT 13980
GGTTTGAGTT TACCCTGCCC GAGGGCAACT TTTCCGAGAC CATGACCATA GACCTGATGA 14040
ACAACGCCAT CTTGGAAAAC TACTTGCAAG TGGGCGGCA AAATGGCGTG CTGGAGAGCG 14100
ATATTGGAGT CAAGTTTGAC AGCAGAAATT TCAAGCTGGG CTGGACCCT GTGACCAAGC 14160
TGGTGATGCC AGGGGTCTAC ACCTACGAGG CCTTTCACCC GGACGTGGTG CTGCTGCCGG 14220
GCTGCGGGGT GGACTTCACA GAGAGCCGCC TGAGCAACCT CCTGGGCATT CGCAAGAAGC 14280
AACCTTTCCA AGAGGGCTTC AGAATCATGT ATGAGGATCT AGAAGGGGGC AACATCCCCG 14340
CCCTGCTGGA TGTGCCCAAG TACTTGGAAA GCAAGAAGAA GTTAGAGGAG GCATTGGAGA 14400
ATGCTGCTAA AGCTAATGGT CCTGCAAGAG GAGACAGTAG CGTCTCAAGA GAGGTTGAAA 14460
```

```
AGGCAGCTGA  AAAAGAACTT  GTTATTGAGC  CCATCAAGCA  AGATGATACC  AAGAGAAGTT  14520
ACAACCTCAT  CGAGGGAACC  ATGGACACGC  TGTACCGCAG  CTGGTACCTG  TCCTATACCT  14580
ACCGGGACCC  TGAGAACGGG  GTGCAGTCGT  GGACGCTGCT  CACCACCCCG  GACGTCACCT  14640
GCGGCGCGGA  GCAAGTCTAC  TGGTCGCTGC  CGGACCTCAT  GCAAGACCCC  GTCACCTTCC  14700
GTTCTACCCA  GCAAGTCAGC  AACTACCCCG  TGGTCGGCGC  CGAGCTCATG  CCCTTCCGCG  14760
CCAAGAGCTT  TTACAACGAC  CTCGCCGTCT  ACTCCCAGCT  CATCCGCAGC  TACACCTCCC  14820
TCACCCACGT  CTTCAACCGC  TTCCCCGACA  ACCAGATCCT  CTGCCGTCCG  CCCGCGCCCA  14880
CCATCACCAC  CGTCAGTGAA  AACGTGCCTG  CTCTCACAGA  TCACGGGACG  CTACCGCTGC  14940
GCAGCAGTAT  CCGCGGAGTC  CAGCGAGTGA  CCGTCACTGA  CGCCCGTCGC  CGCACCTGTC  15000
CCTACGTCTA  CAAGGCCCTG  GGCATAGTCG  CGCCGCGTGT  GCTTTCCAGT  CGCACCTTCT  15060
AAAAAATGTC  TATTCTCATC  TCGCCCAGCA  ATAACACCGG  CTGGGGTATT  ACTAGGCCCA  15120
GCAGCATGTA  CGGAGGAGCC  AAGAAACGTC  CCAGCAGCAC  CCCGTCCGCG  TCCGCGGCCA  15180
CTTCCGCGCT  CCGTGGGGCG  CTTACAAGCG  CGGGCGGACT  GCCACCGCCG  CCGCCGTGCG  15240
CACCACCGTC  GACGACGTCA  TCGACTCGGT  GGTCGCCGAC  GCGCGCAACT  ATACTCCCGC  15300
CCCTTCGACC  GTGGACGCGG  TTCATTGACA  GCGTGGTGGC  GACGCGGCGG  CGATATGCCA  15360
GACGCAAGAG  CCGGCGGGCG  GACGGATCGC  CCAGGCGCCA  TTCGGAGCAC  GCCCGCCATG  15420
GGGCGCCGCC  CGAGCTCTGC  TGCGCCGCGC  CAGACGCACG  GGCCGCCGGG  CCATGATGCG  15480
AGCCGCGCGC  CGCGCCGCCA  CTGCACCCCC  CGCAGGCAGG  ACTCGCAGAC  GAGCGGCCGC  15540
CGCCGCCGCC  GCGGCCATCT  CTAGCATGAC  CAGACCCAGG  CGCGGAAACG  TGTACTGGGT  15600
GCGCGACTCC  GTCACGGGCG  TGCGCGTGCC  CGTGCGCACC  CGTCCTCCTC  TCCCTGATCT  15660
AATGCTTGTG  TCCTCCCCCG  CAAGCGACGA  TGTCAAAGCG  CATCTACAAG  AGAGATGCTC  15720
CAGGTCGTCG  CCCCGGAGAT  TTACGGACCA  CCCCAGGCGG  ACCAGAAACC  CCGCAAAATC  15780
AAGCGGGTTA  AAAAAAAGGA  TGAGGTGGAC  GAGGGGGCAG  TAGAGTTTGT  GCGCGAGTTC  15840
GCTCCGCGGC  GGCGCGTAAA  TTGGAAGGGG  CGCAGGTGCA  CGCGTGTTGC  GGCCCGGCAC  15900
GGCGGTGGTG  TTCACGCCCG  GCGAGCGGTC  CTCGGTCAGG  AGCAAGCGTA  GCTATGACGA  15960
GGTGTACGGC  GACGACGACA  TCCTGGACCA  GGCGGCAGAG  CGGGCGGGCG  AGTTTGCCTA  16020
CGGGAAGCGG  TCGCGCGAAG  AGGAGCTGAT  CTCGCTGCCG  CTGGACGAGA  GCAATCCCAC  16080
GCCGAGCCTG  AAGCCCGTGA  CCTGCAGCAG  GTGCTGCCCC  AGGCGGTGCT  GCTGCCGAGC  16140
CGCGGGATCA  AGCGCGAGGG  CGAGAACATG  TACCCGACCA  TGCAGATCAT  GGTGCCCAAG  16200
CGCCGGCGCG  TGGAGGAAGT  GCTGGACACC  GTGAAAATGG  ATGTGGAGCC  CGAGGTCAAG  16260
GTGCGCCCCA  TCAAGCAGGT  GGCGCCGGGC  CTGGGCGTGC  AGACCGTGGA  CATTCAGATC  16320
CCCACCGACA  TGGATGTCGA  CAAAAAACCC  TCGACCAGCA  TCGAGGTGCA  GACCGACCCC  16380
TGGCTCCCAG  CCTCCACCGC  TACCCTTCCA  CTTCTACCGT  CGCCACGGTC  ACCGAGCCTC  16440
CCAGGAGGCG  AAGATGGGGC  CCCGCCAACC  GGCTGATGCC  CAACTACGTG  TTGCATCCTT  16500
CCATTATCCC  GACGCCGGGC  TACCGCGGCA  CCCGGTACTA  CGCCAGCCGC  AGGCGCCCAG  16560
CCAGCAAACG  CCGCCGCCGC  ACCGCCACCC  GCCGCCGTCT  GCCCCCCGCC  CGCGTGCGCC  16620
GCGTAACCAA  CGCGCCGGGG  CCGCTCGCTC  GTTCTGCCCA  CCGTGCGCTA  CCACCCCAGC  16680
ATCCTTTAAT  CCGTGTGCTG  TGATACTGTT  GCAGAGAGAT  GGCTCTCACT  TGCCGCCTGC  16740
GCATCCCCGT  TCCGAATTAC  CGAGGAAGAT  CCCGCCGCAG  GAGAGGCATG  GCAGGCAGCG  16800
GCCTGAACCG  CCGCCGGCGG  CGGGCCATGC  GCAGGCGCCT  GAGTGGCGGC  TTTCTGCCCG  16860
```

-continued

```
CGCTCATCCC CATAATCGCG GCGGCCATCG GCACGATCCC GGGCATAGCT TCCGTTGCGC    16920
TGCAGGCGTC GCAGCGCCGT TGATGTGCGA ATAAAGCCTC TTTAGACTCT GACACACCTG    16980
GTCCTGTATA TTTTTAGAAT GGAAGACATC AATTTTGCGT CCCTGGCTCC GCGGCACGGC    17040
ACGCGGCCGT TCATGGGCAC CTGGAACGAG ATCGGCACCA GCCAGCTGAA CGGGGGCGCC    17100
TTCAATTGGA GCAGTGTCTG GAGCGGGCTT AAAAATTTCG GCTCGACGCT CCGGACCTAT    17160
GGGAACAAGG CCTGGAATAG TAGCACGGGG CAGTTGTTGA GGGAAAAGCT CAAAGACCAG    17220
AACTTCCAGC AGAAGGTGGT GGACGGCCTG GCCTCGGGCA TTAACGGGGT GGTGGACATC    17280
GCGAACCAGG CAGTGCAGCG CGADATAAAC AGCCGTCTGG ACCCGCGGCC GCCCACGGTG    17340
GTGGAGATGG AAGATGCAAC TCTTCCGCCG CCGAAGGGCG AGAAGCGGCC GCGGCCAGAT    17400
GCGGAGGAGA CGATCCTGCA GGTGGACGAG CCGCCTTCGT ACGAGGAGGC CGTGAAGGCC    17460
GGCATGCCCA CCACGCGCAT CATCGCGCCA CTGGCCACGG GTGTAATGAA ACCCGCCACC    17520
CTTGACCTGC CTCCACCACC CACGCCCGCT CCACCGAAGG CAGCTCCGGT TGTGCAGCCC    17580
CCTCCGGTGG CGACCGCCGT GCGCCGCGTC CCCGCCCGCC GCCAGGCCCA GAACTGGCAG    17640
AGCACGCTGC ACAGTATTGT GGGCCTGGGA GTGAAAAGTC TGAAGCGCCG CCGATGCTAT    17700
TGAGAGAGAG GAAGGAGGAC ACTAAAGGGA GAGCTTAACT TGTATGTGCC TTACCGCCAG    17760
AGAACGCGCG AAGATGGCCA CCCCCTCGAT GATGCCGCAG TGGGCGTACA TGCACATCGC    17820
CGGGCAGGAC GCCTCGGAGT ACCTGAGCCC GGGTCTGGTG CAGTTTGCCC GCGCCACCGA    17880
CACGTACTTC AGCCTGGGCA ACAAGTTTAG GAACCCCACG GTGGCCCCGA CCCACGATGT    17940
GACCACGGAC CGGTCCCAGC GTCTGACGCT GCGCTTTGTG CCCGTGGATC GCGAGGACAC    18000
CAGTACTCGT ACAAGGCGCG CTTCACTCTG GCCGTWGCGA CAACCGGGTG CTAGACATGG    18060
CCAGCACGTA CTTTGACATC CGCGGCGTCC TGGACCGCGG TCCCAGTTTC AAACCCTACT    18120
CGGGCACGGC TTACAACAGC CTTGCCCCCA AGGGCGCTCC CAATCCCAGT CAGTGGGTTG    18180
CCAAAGAAAA TGGTCAGGGA ACTGATAAGA CACATACTTA TGGCTCAGCT GCCATGGGAG    18240
GAAGCAACAT CACCATTGAA GGTTTAGTAA TTGGAACTGA TGAAAAAGCT GAGGATGGCA    18300
AAAAGATAT TTTTGCAAAT AAACTTTATC AGCCAGAACC TCAAGTAGGT GAAGAAAACT    18360
GGCAAGAGTC TGAAGCCTTC TATGGAGGCA GAGCTCTTAA GAAAGACACA AAAATGAAGC    18420
CCTGCTATGG CTCATTTGCA AGACCTACCA ATGAAAAAGG CGGACAAGCT AAATTTAAGC    18480
CAGTGGAAGA GGGGCAGCAA CCTAAAGATT ATGACATAGA TTTGGCTTTC TTTGACACAC    18540
CTGGAGGCAC CATCACAGGA GGCACAGACG AAGAATATAA AGCAGACATT GTGTTGTACA    18600
CTGAAAATGT CAACCTTGAA ACCCAGACA CCCACGTGGT ATACAAGCCA GGAAAAGAGG    18660
ATGACAGTTC AGAAGTAAAT TTGACACAGC AGTCCATGCC CAACAGGCCT AACTACATTG    18720
GCTTCAGAGA CAACTTTGTG GGACTCATGT ACTACAACAG TACTGGCAAC ATGGGTGTGC    18780
TGGCTGGTCA GGCCTCTCAA TTGAATGCTG TGGTCGACTT GCAAGACAGA AACACCGAGC    18840
TGTCTTACCA GCTCTTGCTA GATTCTCTGG GTGACAGAAC CAGATACTTC AGCATGTGGA    18900
ACTCTGCGGT GGATAGCTAT GATCCAGATG TCAGGATCAT TGAAAATCAT GGTGTGGAAG    18960
ATGAACTTCC AAACTATTGC TTCCCATTGA ATGGCACTGG CACCAATTCA ACATATCTTG    19020
GCGTAAAGGT GAAACCAGAT CAAGATGGTG ATGTTGAAAG CGAGTGGGAT AAAGATGATA    19080
CCATTCCAAG GCAGAATCAA ATCGCCAAGG GCAACGTCTT TGCCATGGAG ATCAACCTCC    19140
AGGCCAACCT GGGAAGAGTT TTCTGTACTC GAACGTGGCC TTGTACCTGC CCGACTCCTA    19200
CAAGTACACG CCGGCCAATG TTACGCTGCC CGCCAACACC AACACCTACG AGTACATGAA    19260
```

```
CGGCCGCGTG GTAGCCCCCT CGCTGGTGGA CGCCTACATC AACATAGGCG CCCGATGGTC    19320
GCTGGACCCC ATGGACAACG TCAACCCCTT CAACCACCAC CGCAATGCGG GCCTGCWTAC    19380
CGCTCCATGC TTCTGGGCAA CGGCCGCTAC GTGCCCTTCC ACATCCAAGT GCCCCAAAAG    19440
TTCTTTGCCA TCAAGAACCT GCTCCTGCTC CCGGGCTCCT ACACCTACGA GTGGAACTTC    19500
CGCAAGGATG TCAACATGAT CCTGCAGAGT TCCCTCGGCA ACGACCTGCG CGTCGACGGC    19560
GCCTCCGTCC GCTTCGACAG CGTCAACCTC TACGCCCCTT CTTCCCCATG GCGCACAACA    19620
CCGCCTCCAC CCTGGAAGCC ATGCTGCGCA ACGACACCAA CGACCAGTCC TTCAACGACT    19680
ACCTCTCGGC CGCCAACATG CTCTACCCCA TCCCGGCCAA GGCCACCAAC GTGCCCATCT    19740
CCATCCCCTC GCGCAACTGG GCCGCTTTTC GCGGCTGGAG TTTCACCCGT CTGAAAACCA    19800
AGGAAACTCC CTCCCTCGGC TCGGGTTTTG ACCCCTACTT TGTCTACTCG GCTCGATCC    19860
CCTACCTTGA CGGACCCTTT TACCTTAACC ACACCTTCAA GAAAGTCTCC ATCATGTTCG    19920
ACTCCTCGGT CAGCTGGCCC GGCAACGACC GGCTGCTCAC GCCGAACGAG TTCGAGATCA    19980
AGCGCAGCGT CGACGGGGAA GGCTACAACG TGGCCCAATG CAACATGACC AAGGACTGGT    20040
TCCTCGTCCA GATGCTCTCC CACTACAACA TCGGCTACCA GGGCTTCCAC GTGCCCGAGG    20100
GCTACAAGGA CCGCATGTAC TCCTTCTTCC GCAACTTCCA GCCCATGAGC AGGCAGGTGG    20160
TCGATGAGAT CAACTACAAG GACTACAAGG CCGTCACCCT GCCCTTCCAG CACAACAACT    20220
CGGGCTTCAC CGGCTACCTT GCACCCACCA TGCGCCAAGG GCAGCCCTAC CCCGCCAACT    20280
TCCCCTACCC GCTCATCGGC CAGACAGCCG TGCCATCCGT CACCCAGAAA AGTCTCCTCT    20340
GCGACAGGGT CATGTGGCGC ATCCCCTTCT CCAGCAACTT CATGTCCATG GGCGCCTTCA    20400
CCGACCTGGG TCAGAACATG TTCTACGCCA ACTCGGCCCA CGCGCTCGAC ATGACCTTCG    20460
AGGTGGACCC CATGGATGAG CCCACCGTCC TCTATCTTCT CTTCGAAGTG TTCGACGTGG    20520
TCAGAGTGCA CCAGCCGCAC CGCGGCGTCA TCGAGGCCGT CTACCTGCGC ACGCCGTTCT    20580
CCGCCGGAAA CGCCACCACC TAAGCATGAG CGGCTCCAGC GAAAGAGAGC TCGCGTCCAT    20640
CGTGCGCGAC CTGGGCTGCG GGCCTACTTT TTGGGCACCC ACGACACAGC GATTCCCGGG    20700
CTTTCTTGCC GGCGACAAGC TGGCCTGCGC CATTGTCAAC ACGGCCGGCC GCGAGACCGG    20760
AGGCGTGCAC TGGCTCGCCT TCGGCTGGAA CCCGCGCTCG CGCACCTGCT ACATGTTCGA    20820
CCCCTTTGGG TTCTCGGACC GCCGGCTCAA GCAGATTTAC AGCTTCGAGT ACGAGGCCAT    20880
GCTGCGCCGA AGCGCCGTGG CCTCTTCGCC CGACCGCTGT CTCAGCCTCG AACAGTCCAC    20940
CCAGACCGTG CAGGGGCCCG ACTCCGCCGC CTGCGGACTT TTCTGTTGCA TGTTCTTGCA    21000
TGCCTTCGTG CACTGGCCCG ACCGACCCAT GGACGGGAAC CCCACCATGA ACTTGCTGAC    21060
GGGGGTGCCC AACGGCATGC TACAATCGCC ACAGGTGCTG CCCACCCTCA GGCGCAACCA    21120
GGAGGAGCTC TATCGCTTCC TCGCGCGCCA CTCCCCTTAC TTTCGCTCCC ACCGCGCCGC    21180
CATCGAACAC GCCACCGCTT TTGACAAAAT GAAACAACTG CGTGTATCTC AATAAACAGC    21240
ACTTTTATTT TACATGCACT GGAGTATATG CAAGTTATTT AAAAGTCGAA GGGGTTCTCG    21300
CGCTCATCGT TGTGCGCCGC GCTGGGGAGG CCACGTTGC GGTACTGGTA CTTGGGCTGC    21360
CACTTGAACT CGGGGATCAC CAGTTTGGGC ACTGGGGTCT CGGGGAAGGT CTCGCTCCAC    21420
ATACGCCGGC TCATCTGCAG GGCGCCCAGC ATGTCCGGGG CGGATATCTT GAAATCGCAG    21480
TTGGGACCGG TGCTCTGCGC GCGCGAGTTG CGGTACACGG GGTTGCAGCA CTGGAACACC    21540
ATCAGACTGG GGTACTTTAC GCTGGCCAGC ACGCTCTTGT CGCTGATCTG ATCCTTGTCC    21600
AGATCCTCGG CGTTGCTCAC GCCGAATGGG GTCATCTTGC ACAGTTGGCG ACCCAGGAAT    21660
```

```
GGCACGCTCT GAGGCTTGTG GTTACACTCG CAGTGCACGG GCATCAGCAT CATCCCCGCG 21720
CCGCGCTGCA TATTCGGGTA GAGGCCTTGA CAAAGGCCGT GATCTGCTTG AAAGCTTGTT 21780
GGGCCTTGGC CCCCTCGCTG AAAAACAGGC CGCAGCTCTT CCCGCTGAAC TGGTTATTCC 21840
CGCACCCGGC ATCCTGCACG CAGCAGCGCG CGTCATGGCT GGTCAGTTGC ACCACGCTTC 21900
TTCCCCAGCG GTTCTGGGTC ACCTTGGCTT TGCTGGGTTG CTCCTTCAAC GCGCGCTGCC 21960
CGTTCTCGCT GGTCACATCC ATCTCCACCA CGTGGTCCTT GTGGATCATC ACCGTTCCAT 22020
GCAGACACTT GAGCTGGCCT TCCACCTCGG TGCAGCCGTG ATCCCACAGG GCACTGCCGG 22080
TGCACTCCCA GTTCTTGTGC GCGATCCCGC TGTGGCTGAA GATGTAACCT GCAAGAGGC 22140
GACCCATGAT GGTGCTAAAG CTCTTCTGGG TGGTGAAGGT TAGTTGCAGA CCGCGGGCCT 22200
CCTCGTTCAT CCAGGTCTGG CACATCTTTT GGAAGATCTC GGTCTGCTCG GCATGAGCT 22260
TGTAAGCATC GCGCAGGCCG CTGTCGACGC GGTAACGTTC CATCAGCACG TTCATGGTAT 22320
CCATGCCCTT TTCCCAGGAC GAGACCAGAG GCAGACTCAG GGGGTTGCGC ACGTTCAGGA 22380
CACCGGGGGT CKCGGGCTCG ACGATACGTT TTCCGTCCTT GCCTTCCTTC AACAGAACCG 22440
GAGGCTGGCT GAATCCCACT CCCACAATCA CGGCATCTTC CGGGGCATCT CTTCGTCGGG 22500
GTCTACCTTG GTCACATGCT TGGTCTTTCT GGCTTGCTTC TTTTTGGAG GCTGTCCAC 22560
GGGGACCACG TCCTCTCGGA AGACCCGGAG CCCACCCGCT GATACTTTCG GCGCTTGGTG 22620
GGCAGAGGAG GTGGCGGCGG CGAGGGGCTC CTCTCGTGCT CCGGCGGATA GCGCGCCGAC 22680
CCGTGGCCCC GGGGCGGAGT GGCCTCTCGC TCCATGAACC GGCGCACGTC TGACTGCCGC 22740
CGGCCATTGT TTCCTAGGGG AAGATGGAGG AGCAGCCGCG TAAGCAGGAG CAGGAGGAGG 22800
ACTTAACCAC CCACGAGCAA CCCAAAATCG AGCAGGACCT GGGCTTCGAA GAGCCGGCTC 22860
GTCTAGAACC CCACAGGATG AACAGGAGCA CGAGCAAGAC GCAGGCCAGG AGGAGACCGA 22920
CGCTGGGCTC GAGCATGGCT ACCTGGGAGG AGAGGAGGAT GTGCTGCTGA AACACCTGCA 22980
GCGCCAGTCC CTCATCCTCC GGGACGCCCT GGCCGACCGG AGCGAAACCC CCTCAGCGT 23040
CGAGGAGCTG TGTCGGGCCT ACGAGCTCAA CCTCTTCTCG CCGCGCGTGC CCCCAAACG 23100
CCAGCCCAAC GGCACCTGCG AGCCCAACCC GCGTCTCAAC TTCTATCCCG TCTTTGCGGT 23160
CCCCGAGGCC CTTGCCACCT ATCACATCTT TTTCAAGAAC CAAAAGATCC CCGTCTCCTG 23220
CCGCGCCAAC CGCACCCGCG CCGACGCGCT CCTCGCTCTG GGCCCGGCG CGCGCATACC 23280
TGATATTGCT TCCCTGGAAG AGTGCCCAAA ATCTTCGAAG GGCTCGGTCG GGACGAGACG 23340
CGCGCGGCGA AACGCTCTGA AAGAAACAGC AGAGGAAGAG GGTCACACTA GCGCCCTGGT 23400
AGAGTTGGAA GGCGACAACG CCAGGCTGGC CGTGCTCAAG CGCAGCGTTG AGCTCACCCA 23460
CTTCGCCTAC CCCGCCGTCA ACCTCCCGCC CAAGGTCATG CGTCGCATCA TGGATCAGCT 23520
AATCATGCCC CACATCGAGG CCCTCGATGA AAGTCAGGAG CAGCGCCCCG AGGACACCCG 23580
GCCCGTGGTC AGCGATGAGC AGCTTGCGCG CTGGCTTGGT ACCCGCGACC CCAGGCCCT 23640
GGAGCAGCGG CGCAAGCTCA TGCTGGCCGT GGTCCTGGTC ACCCTCGAGC TCGAATGCAT 23700
GCGACGCTTT TTCAGCGACC CCGAGACCTG CGCAAGGTCG AGGAGACCTG CACTACACTT 23760
TTAGCACGTT TCGTCAGGCA GGCATGCAAG ATCTCCAACG TGGAGCTGAC CAACTGGTCT 23820
CCTGCCTGGG AATCCTGCAC GAGAACCGCC TGGGCAGAC AGTGCTCCAC TCGACCCTGA 23880
AGGGCGAGGC GCGGCGGGAC TATGTCCGCG ACTGCGTCTT TCTCTTTCTC TGCCACACAT 23940
GGCAAGCTGC CATGGGCGTG TGGCAGCAGT GTCTCGAGGA CGAGAACCTG AAGGAGCTGG 24000
ACAAGCTTCT TGCTAGAAAC CTCAAAAAGC TGTGGACGGG CTTTGACGAG CGCACCGTCG 24060
```

```
CCTCGGACCT  GGCCGAGATC  GTCCTCCCCC  GAGCGCCTGA  GGCAGACGCT  GAAAGGCGGG   24120

CTGCCCGACT  TCATGAGCCA  GAGCATGTTG  CAAAACTACC  GCACTTTCAT  TCTCGAGCGA   24180

TCTGGGATGC  TGCCCGCCAC  CTGCAACGCC  TTCCCCTCCG  ACTTTGTCCC  GCTGAGCTAC   24240

CGCGAGTGTC  CCCCGCCGCT  GTGGAGCCAC  TGCTACCTCT  TGCAGCTGGC  CAACTACATC   24300

GCCTACCACT  CGGATGTTAT  CGAGGACGTG  AGCGGCGAGG  GGCTGCTAGA  GTGCCACTGC   24360

CGCTGCAACC  TGTGCTCTCC  GCACCGCTCC  TGGTCTGCAA  CCCCCAGCTC  CTGAGCGAGA   24420

CCCAGGTCAT  CGGTACCTCG  AGCTGCAAGG  TCCGCAGGAG  TCCACCGCTC  CGCTGAAACT   24480

CACGCCGGGG  TTGTGGACTT  CCGCGTACCT  GCGCAAATTT  GTACCCGAGG  ACTACCACGC   24540

CCATGAGATA  AAGTTCTTCG  AGGACCAATC  GCGCCCGCAG  CACGCGGATC  TCACGGCCTG   24600

CGTCATCACC  CAGGGCGCGA  TCCTCGCCCA  ATTGCACGCC  ATCCAAAAAT  CCCGCCAAGA   24660

GTTTCTTTTG  AAAAAGGGTA  GAGGGGTCTA  TCTGGACCCC  CAGACGGGCG  AAGTGCTCAA   24720

CCCGGGTCTC  CCCCAGCATG  CCGAAGAAGA  ACAGGAGCCG  CTAGTGGAAG  AGATGGAAGA   24780

AGAATGGGAC  AGCCAGCAGA  AGAAGACGAA  TGGGAAGAAG  AGACAGAAGA  AGAAGAATTG   24840

GAAAAGTGGA  AGAAGAGCAG  CACAGACACC  GTCGCCGCAC  CATCCGCGCC  GCAGCCCGGC   24900

GGTCACGGAT  ACAACTCGCA  GTCCGCCAAG  CTCCTCGTAG  ATGGATCGAG  TGAAGGTGAC   24960

GGTAAGCACG  AGCGGCAGGG  CTACGAATCA  TGGAGGCCCA  CAAAGCGGGA  TCATCGCCTG   25020

CTTGCAAGAC  TGCGGGGGGA  ACATCGTTTC  GCCCGCCGCT  ATCTGCTCTT  CCATCGCGGG   25080

GTGAACATCC  CCCGCAACGT  GTTGCATTAC  TACCGTCACC  TTCACAGCTA  AGAAAAAATC   25140

AGAGTAAGAG  GAGTCGCCGG  AGGAGGCNTG  AGGATCGCGG  CGAACGAGCC  ATTGACCACC   25200

AGGGAGCTGA  GGAATCGGAT  CTTCCCCACT  CTTTATGCCA  TTTTTCAGCA  GAGTCGAGGT   25260

CAGCAGCAAG  AGCTCAAAGT  AAAAAACCGG  TCTCTGCGCT  CGCTCACCCG  CAGTTGCTTG   25320

TACCACAAAA  ACGAAGATCA  GCTGCAGCGC  ACTCTCGAAG  ACGCCGAGGC  TCTGTTCCAC   25380

AAGTACTGCG  CGCTCACTCT  TAAAGACTAA  GGCGCGCCCA  CCCGGAAAAA  AGGCGGGAAT   25440

TACCTCATCG  CCACCATGAG  CAAGGAGATT  CCCACCCCTT  ACATGTGGAG  CTATCAGCCC   25500

CAGATGGGCC  TGGCCGCGGG  CGCCTCCCAG  GACTACTCCA  CCCGCATGAA  CTGGCTCAGT   25560

GCCGGCCCCT  CGATGATCTC  ACGGGTCAAC  GGGGTCCGTA  CCATCGAAA   CCAGATATTG   25620

TTGGAGCAGG  CGGCGGTCAC  CTCAACGCCC  AGGCAAAGCT  CAACCCGCGT  AATTGGCCCT   25680

CCACCCTGGT  GTATCAGGAA  ATCCCCGGGC  CGACTACCGT  ACTACTTCCG  CGTGACGCAC   25740

TGGCCGAAGT  CCGCATGACT  AACTCAGGTG  TCCAGCTGGC  CGGCGGCGCT  TCCCGGTGCC   25800

CGCTCCGCCC  ACAATGGGT   ATAAAAACCC  TGGTGATACG  AGGCAGAGGC  ACACAGCTCA   25860

ACGACGAGTT  GGTGAGCTCT  TCAATCGGTC  TGCGACCGGA  CGGAGTGTTC  CAACTAGCCG   25920

GAGCCGGGAG  ATCGTCCTTC  ACTCCCAACC  AGGCTACCTG  ACCTTGCAGA  GCAGCTCTTC   25980

GGAGCCTCGC  TCCGGAGGCA  TCGGAACCCT  CCAGTTTGTG  GAGGAGTTTG  TGCCCTCGGT   26040

CTACTTCAAC  CCCTTCTCGG  GATCGCCAGG  CCTCTACCCG  GACGAGTTCA  TACCGAACTT   26100

CGACGCAGTG  AGAGAAGCGG  TGGACGGCCA  CGACTGAATG  TCTTATGGTG  ACTCGGCTGA   26160

GCTCGCTCGG  TTGAGGCACC  TAGACCACTG  CCGCCGCCTG  CGCTGCTTCG  CCCGGGAGAG   26220

CTGCGGACTT  ATCTACTTTG  AGTTTCCCGA  GGAGCACCCC  AACGGCCCTG  CACACGGAGT   26280

GCGGATCACC  GTAGAGGGCA  CCACCGAGTC  TCACCTGGTT  AGGTTCTTCA  CCCAGCAACC   26340

CTTCCTGGTC  GAGCGGGACC  GGGGAGGCAC  CACCTACACC  GTCTACTGCA  TCTGTCCAAC   26400

CCCGAAGTTG  CATGAGAATT  TTTGTTGTAC  TCTGTGTGCT  GAGTTTAATA  AAAGCTAAAC   26460
```

```
TCCTACAATA CTCTGGGATC CCGTGTCGTC GCACTCGCAA CAAGACCTTC AACCTCACCA    26520
ACCAGACTGA GGTAAAATTC AACTGCAGAC CGGGGGACAA ATACATCCTC TGGCTTTTTA    26580
AAAACACTTC CTTCGCAGTC TCCAACGCCT GCGCCAACGA CGGTATTGAA ATACCCAACA    26640
ACCTTACCAG TGGACTAACT TATACTACCA GAAAGACTAA GCTAGTACTC TACAATCCTT    26700
TTGTAGAGGG AACCTACCAC TGCCAGAGCG GACCTTGCTT CCACACTTTC ACTTTGGTGA    26760
ACGTTACCGA CAGCAGCACA GCCGCTACAG AAACATCTAA CCTTCTTTTT GATACTAACA    26820
CTCCTAAAAC CGGAGGTGAG CTCTGGGTTC CCTCTCTAAC AGAGGGGGT  AAACATATTG    26880
AAGCGGTTGG GTATTTGATT TTAGGGGTGG TCCTGGGTGG GTGCATAGCG GTGCTGTATT    26940
ACCTTCCTTG CTGGATCGAA ATCAAAATCT TTATCTGCTG GGTCAGACAT TGTTGGGAGG    27000
AACCATGAAG GGGCTCTTGC TGATTATCCT TTCCCTGGTG GGGGGTGTAC TGTCATGCCA    27060
CGAACAGCCA CGATGTAACA TCACCACAGG CAATGAGAGG AGTGTGATAT GCACAGTAGT    27120
CATCAAATGC GAGCATACAT GCCCTCTCAA CATCACATTC AAAAACCGTA CCATGGGAAA    27180
TGCATGGGTG GGCGACTGGG AACCAGGAGA TGAGCAGAAC TACACGGTCA CTGTCCATGG    27240
TAGCAATGGA AATCACACTT TTGGTTTCAA ATTCATTTTT GAAGTCATGT GTGATATCAC    27300
ACTGCATGTG GCTAGACTTC ATGGCTTGTG GCCCCCTACC AAGGATAACA TGGTTGGGTT    27360
TTCTTTGGCT TTTGTGATCA TGGCCTGTGC AATGTCAGGT CTGCTGGTAG GGGCTTTAGT    27420
GTGGTTCCTA AAGCGCAAGC CTAGGTATGG AAATGAGGAG AAGGAAAAAT TGCTATAAAT    27480
CTTTTCTCTT CGCAGAACCA TGAATACAGT GATCCGTATC GTGCTGCTCT CTCTTCTTGT    27540
AACTTTTAGT CAGGCAGGAT TCATACCATC AATGCTACAT GGTGGGCTAA TATAACTTTA    27600
GTGGGACCTC AGATATTCCA GATCACATGG TATGATAGCA CTGGATTGCA ATTTTGTGAT    27660
GGAAGTACAG TTAAGAATCC ACAGATCAGA CATAGTTGTA ATGATCAAAA CTTAACTCTG    27720
ATTCATGTGA ACAAAACCCA TGAAAGAACA TACATGGGCT ATAATAAGCA GAGTACTCAT    27780
AAAGAAGACT ATAAAGTCAC AGTTATACCA CCTCCTCCTG TTACTGTAAA GCCACAACCA    27840
GAGCCAGAAT ATGTGTATGT TAATATGGGA GAGAACAAAA CCTTAGTTGG GCCTCCAGGA    27900
ATTCCAGTTA GTTGGTTTAA TCAGGATGGT TTACAATTTT GCATTGGGGA TAAAGTTTTT    27960
CATCCAGAAT TCAACCACAC CTGTGACATG CAAAATCTTA CACTGTTGTT TATAAATCTT    28020
ACACATGATG GAGCTTATCT TGGTTATAAT CGCCAGGGAA CTGAAAGAAC TTGGTATGAG    28080
GTTGTAGTGT CAGATGGTTT TCCAAAATCA GAAGAGATGA AGGTAGAAGA CCATAGTAAA    28140
GAAACAGAAC AAAAACAGAC TGGTCAAAAA CAAAGTGACC ATAAGCAGGG TGGGCAAAAA    28200
GAAACAAGTC AAAAGAAAAC TAATGACAAA CAAAAGCCAT CGCGCAGGAG GCCATCTAAA    28260
CTAAAGCCAA ACACACCTGA CACAAAACTA ATTACAGTCA CTAGTGGGTC AAACGTAACT    28320
TTAGTTGGTC CAGATGGAAA GGTCACTTGG TATGATGATG ATTTAAAAG  ACCATGTGAG    28380
CCTGGGTATA AGTTAGGGTG TAAGTGTGAC AATCAAAACC TAACCCTAAT CAATGTAACT    28440
AAACTTTATG AGGGAGTTTA CTATGGTACT AATGACAGAG GCAACAGCAA AGATACAGA    28500
GTAAAAGTAA ACACTACTAA TTCTCAAAGT GTGAAAATTC AGCCGTACAC CAGGCCTACT    28560
ACTCCTGATC AGAAACACAG ATTTGAATTG CAAATTGATT CTAATCAAGA CAAAATTCCA    28620
TCAACTACTG TGGCAATCGT GGTGGGAGTG ATCGCGGGCT TTGTAACTCT AATCATTATT    28680
TTCATATGCT ACATCTGCTG CCGCAAGCGT CCCAGGTCAT ACAATCATAT GGTAGACCCA    28740
CTACTCAGCT TCTCTTACTG AAACTCAGTC ACTCTCATTT CAGAACCATG AAGGCTTTCA    28800
CAGCTTGCGT TCTGATTAGC ATAGTCACAC TTAGTTCAGC TGCAATGATT AATGTTAATG    28860
```

```
TCACTAGAGG TGGTAAAATT ACATTGAATG GGACTTATCC ACAAACTACA TGGACAAGAT    28920
ATCATAAAGA TGGATGGAAA AATATTTGTG AATGGAATGT TACTGCATAC AAATGCTTCA    28980
ATAATGGAAG CATTACTATT ACTGCCACTG CCAACATTAC TTCTGGCACA TACAAAGCTG    29040
AAAGCTATAA AAATGAAATT AAAAAATTAA CCTATAAAAA CAACAAAACC ACATTTGAAG    29100
ATTCTGGAAA TTATGAGCAT CAAAAATTAT CTTTTATAT  GTTGACAATA ATTGAACTGC    29160
CTACAACCAA GGCACCCACC ACAGTTAGTA CAACTACACA GTCAACTGTT AAGACCACTA    29220
CTCACACTAC ACAGCTAGAC ACCACAGTGC AGAATAATAC TGTGTTGGTT AGGTATTTGT    29280
TGAGGGAGGA AAGTACTACT GAACAGACAG AGGCTACCTC AAGTGCCTTT ATCAGCACTG    29340
CAAATTTAAC TTCGCTTGCT TGGACTAATG AAACCGGAGT ATCATTGATG CATGGCCAGC    29400
CTTACTCAGG TTTGGATATT CAAATTACTT TTCTGGTTGT CTGTGGGATC TTTATTCTTG    29460
TGGTTCTTCT GTACTTTGTC TGCTGTAAAG CCAGAAAGAA ATCTAGGAGG CCCATCTACA    29520
GGCCAGTGAT TGGGGAACCT CAGCCACTCC AAGTGGATGG AGGCTTAAGG AATCTTCTTT    29580
TCTCTTTTAC AGTATGGTGA TCAGCCATGA TTCCTAGTTC TTCCTATTTA ACATCCTCTT    29640
CTGTCTCTTC AACATCTGTG CTGCCTTTGC GGCAGTTTCG CACGCCTCGC CCGACTGTCT    29700
AGGGCCTTTC CCCACCTACT CCTCTTTGCC CTGCTCACCT GCACCTGCGT CTGCAGCATT    29760
GTCTGCCTGG TCATCACCTT CCTGCAGCTC ATCGACTGGT GCTGCGCGCG CTACAATTAC    29820
TTCATCATAG TCCCGAATAC AGGGACGAGA ACGTAGCCAG AATTTTAAGG CTCATATGAC    29880
CATGCAGACT CTGCTCATAC TGCTATCGCT CTTATCCCAT GCCCTCGCTA CTGCTGATTA    29940
CTCTAAATGC AAATTGGCGG ACATATGGAA TTTCTTAGAC TGCTATCAGG AGAAAATTGA    30000
TATGCCCTCC TATTACTTGG TGATTGTGGG AATAGTTATG GTCTGCTCCT GCACTTTCTT    30060
TGCCATCATG ATCTACCCCT GTTTTGATCT TGGATGGAAC TCTGTTGAGG CATTCACATA    30120
CACACTAGAA AGCAGTTCAC TAGCCTCCAC GCCACCACCC ACACCGCCTC CCCGCAGAAA    30180
TCAGTTTCCC ATGATTCAGT ACTTAGAAGA GCCCCCTCCC CGACCCCCTT CCACTGTTAG    30240
CTACTTTCAC ATAACCGGCG GCGATGACTG ACCACCACCT GGACCTCGAG ATGGACGGCC    30300
AGGCCTCCGA GCAGCGCATC CTGCAACTGC GCGTCCGTCA GCAGCAGGAG CGTGCCGCCA    30360
AGGAGCTCCT CGATGCCATC AACATCCACC AGTGCAAGAA GGGCATCTTC TGCCTGGTCA    30420
AACAGGCAAA GATCACCTAC GAGCTCGTGT CCAACGGCAA ACAGCATCGC CTCACCTATG    30480
AGATGCCCCA GCAGAAGCAG AAGTTCACCT GCATGGTGGG CGTCAACCCC ATAGTCATCA    30540
CCCAGCAGTC GGGCGAGACC AACGGCTGCA TCCACTGCTC CTGCGAAAGC CCCGAGTGTA    30600
TCTACTCCCT TCTCAAGACC CTTTGCGGAC TCCGCGACCT CCTCCCCATG AACTGATGTT    30660
GATTAAAAAC CAAAAAAAAC AATCAGCCCC TTCCCCTATC CCAAATTACT CGCAAAAATA    30720
AATCATTGGA ACTAATCATT TAATAAAGAT CACTTACTTG AAATCTGAAA GTATGTCTCT    30780
GGTGTAGTTG TTCAGCAGCA CCTCGGTACC CTCCTCCCAA CTCTGGTACT CCAGTCTCCG    30840
GCGGGCGGCG AACTTTCTCC ACACCTTGAA AGGGATGTCA AATTCCTGGT CCACAATTTT    30900
CATTGTCTTC CCTCTCAGAT GTCAAAGAGG CTCCGGGTGG AAGATGACTT CAACCCCGTC    30960
TACCCCTATG GCTACGCGCG GAATCAGAAT ATCCCCTTCC TCACTCCCCC CTTTGTCTCC    31020
TCCGATGGAT TCAAAAACTT CCCCCCTGGG GTCCTGTCAC TCAAACTGGC TGACCCAATC    31080
ACCATAGCCA ATGGTGATGT CTCACTCAAG GTGGGAGGGG ACTTACTTTG CAAGAAGGAA    31140
GTATGACTGT AGACCCTAAG GCTCCCTTGC AACTTGCAAA CAATAAAAAA CTTGAGCTTG    31200
TTTATGTTGA TCCATTTGAG GTTAGTGCCA ATAAACTTAG TTTAAAAGTA GGACATGGAT    31260
```

```
TAAAAATATT  AGATGACAAA  AGTGCTGGAG  GGTTGAAAGA  TTTAATTGGC  AAACTTGTGG   31320

TTTTAACAGG  GGAAAGGAAT  AGGCACTGAA  AATTTGCAAA  ATACAGATGG  TAGCAGCAGA   31380

GGAATTGGTA  TAAGTGTAAG  AGCAAGAGAA  GGGTTAACAT  TTGACAATGA  TGGATACTTG   31440

GTAGCATGGA  ACCCAAAGTA  TGACACGCGC  ACACTTTGGA  CAACACCAGA  CACATCTCCT   31500

AATTGCAGGA  TTGATAAGGA  GAAGATTCAA  AACTCACTTT  GGTACTTACA  AAGTGTGGAA   31560

GTCAAATATT  AGCTAATGTG  TCTTTGATTG  TGGTGTCAGG  AAAATATCAA  TACATAGACC   31620

ACGCTACAAA  TCCAACTCTT  AAATCATTTA  AATAAAACT   TCTTTTTGAT  AATAAGGTG    31680

TACTTCTCCC  AAGTTCAAAC  CTTGATTCCA  CATATTGGAA  CTTTAGAAGT  GACAATTTAA   31740

CTGTATCTGA  GGCATATAAA  AATGCAGTTG  AATTTATGCC  TAATTGGTA   GCCTACCCAA   31800

AACCTACCAC  TGGCTCTAAA  AAATATGCAA  GGGATATAGT  CTATGGGAAC  ATATATCTTG   31860

GAGGTTTGGC  ATATCAGCCA  GTTGTAATTA  AGGTTACTTT  TAATGAAGAA  GCAGATAGTG   31920

CTTACTCTAT  AACATTTGAA  TTTGTATGGA  ATAAAGAATA  TGCCAGGGTT  GAATTTGAAA   31980

CCACTTCCTT  TACCTTCTCC  TATATTGCCC  AACAATAAAA  GACCAATAAA  CGTGTTTTTT   32040

ATTTCAAATT  TTATGTATCT  TTATTGATTT  TTACACCAGC  GCGAGTAGTC  AATCTCCCAC   32100

CACCAGCCCA  TTTCACAGTG  TACACGGTTC  TCTCAGCACG  GTGGCCTTAA  ATAAGGAAAT   32160

GTTCTGATTA  TTGCGGGAAC  TGGACTTGGG  GTCTATAATC  CACACAGTTT  CCTGACGAGC   32220

CAAACGGGGA  TCGGTGATGA  AATGAAGCCG  TCCTCTGAAA  AGTCATCCAA  GCGGGCCTCA   32280

CAGTCCAGGT  CACAGTCTGG  TGGAACGAGA  AGAACGCACA  GATTCATACT  CGGAAAACAG   32340

GATGGGTCTG  TGCCTCTCCA  TCAGCGCCCT  CAGCAGTCTC  TGCCGCCGGG  GCTCGGTGCG   32400

GCTGCTGCAA  ATGGGATCGG  GATCACAAGT  CTCTCTAACT  ATGATCCCAA  CAGCCTTCAG   32460

CATCAGTCTC  CTGGTGCGTC  GAGCACAGCA  CCGCATCCTG  ATCTCTGCCA  TGTTCTCACA   32520

GTAAGTGCAG  CACATAATCA  CCATGTTATT  CAGCAGCCCA  TAATTCAGGG  TGCTCCAGCC   32580

AAAGCTCATG  TTGGGGATGA  TGGAACCCAC  GTGACCATCG  TACCAGATGC  GGCAGTATAT   32640

CAGGTGCCTG  CCCCTCATGA  ACACACTGCC  CATATACATG  ATCTCTTTGG  GCATGTTTCT   32700

GTTTACAATC  TGGCGGTACC  AGGGGAAGCG  CTGGTTGAAC  ATGCACCCGT  AAATGACTCT   32760

CCTGAACCAC  ACGGCCAGCA  GGGTGCCTCC  CGCCCGACAC  TGCAGGGAGC  CAGGGGATGA   32820

ACAGTGGCAA  TGCAGGATCC  AGCGCTCGTA  CCCGCTCACC  ATCTGAGCTC  TTACCAAGTC   32880

CAGGGTAGCG  GGGCACAGGC  ACACTGACAT  ACATCTTTTT  AAAATTTTA   TTTCCTCTGT   32940

GGTGAGGATC  ATATCCCAGG  GGACTGGAAA  CTCTTGGAGC  AGGGTAAAGC  CAGCAGCACA   33000

TGGTAATCCA  CGGACAGAAC  TTACATTATG  ATAATCTGCA  TGATCACAAT  CGGGCAACAG   33060

GGGATGTTGA  TCAGTCAGTG  AAGCCCTGGT  TTCATCATCA  GATCGTGGTA  AACGGGCCCT   33120

GCGATATGGA  TGATGGCGGA  GCGAGCTGGA  TTGAATCTCG  GTTTGCATTG  TAGTGGATTC   33180

TCTTGCGTAC  CTTGTCGTAC  TTCTGCCAGC  AGAAATGGGC  CCTTGAACAG  CATATACCCC   33240

TCCTGCGGCC  GTCCTTTCGC  TGCTGCCGCT  CAGTCATCCA  ACTGAAGTAC  ATCCATTCTC   33300

GAAGATTCTG  GAGAAGTTCC  TCTGCATCTG  ATGAAATAAA  AAACCCGTCC  ATGCGAATTC   33360

CCCTCATCAC  ATCAGCCAGG  ACTCTGTAGG  CCATCCCCAT  CCAGTTAATG  CTGCCTTGTC   33420

TATCATTCAG  AGGGGCGGT   GGCAGGATTG  GAAGAACCAT  TTTTATTCCA  AACGGTCTCG   33480

AAGGACGATA  AAGTGCAAGT  CACGCAGGTG  ACAGCGTTCC  CCTCCGCTGT  GCTGGTGGAA   33540

ACAGACAGCC  AGGTCAAAAC  CCACTCTATT  TTCAAGGTGC  TCGACCGTGG  CTTCGAGCAG   33600

TGGCTCTACG  CGTACATCCA  GCATAAGAAT  CACATTAAAG  GCTGGCCCTC  CATCGATTTC   33660
```

-continued

```
ATCAATCATC AGGTTACATT CCTGCACCAT CCCCAGGTAA TTCTCATTTT TCCAGCCTTG    33720
GATTATCTCT ACAAATTGTT GGTGTAAATC CACTCCGCAC ATGTTGAAAA GCTCCCACAG    33780
TGCCCCCTCC ACTTTCATAA TCAGGCAGAC CTTCATAATA GAAACAGATC CTGCTGCTCC    33840
ACCACCTGCA GCGTGTTCAA AACAACAAGA TTCAATAAGG TTCTGCCCTC CGCCCTGAGC    33900
TCGCGCCTCA ATGTCAGCTG CAAAAAGTCA CTTAAGTCCT GGGCCACTAC AGCTGACAAT    33960
TCAGAGCCAG GGCTAAGCGT GGGACTGGCA AGCGTGAGGG AAAACTTTAA TGCTCCAAAG    34020
CTAGCACCCA AAAACTGCAT GCTGGAATAA GCTCTCTTTG TGTCTCCGGT GATGCCTTCC    34080
AAAATGTGAG TGATAAAGCG TGGTAGTTTT TTCTTTAATC ATTTGCGTAA TAGAAAAGTC    34140
CTGTAAATAA GTCACTAGGA CCCCAGGGAC CACAATGTGG TAGCTTACAC CGCGTCGCTG    34200
AAAGCATGGT TAGTAGAGAT GAGAGTCTGA AAAACAGAAA GCATGCGCTA AACTAAGGTG    34260
GCTATTTTCA CTGAAGGAAA AATCACTCTT TCCAGCAGCA GGGTACCCAC TGGGTGGCCC    34320
TTGCGGACAT ACAAAAATCG GTCCGTGTGA TTAAAAAGCA GCACAGTAAG TTCCTGTCTT    34380
CTTCCGGCAA AAATCACATC GGACTGGGTT AGTATGTCCC TGGCATGGTA GTCATTCAAG    34440
GCCATAAATC TGCCCTGATA TCCAGTAGGA ACCAGCACAC TCACTTTTAG GTGAAGCAAT    34500
ACCACCCCAT GCGGAGGAAT GTGGAAAGAT TCAGGGCAAA AAAAATTATA TCTATTGCTA    34560
GCCCTTCCTG GACGGGAGCA ATCCTCCAGG ACTATCTATG AAAGCATACA GAGATTCAGC    34620
CATAGCTCAG CCCGCTTACC AGTAGACAAA GAGCACAGCA GTACAAGCGC CAACAGCAGC    34680
GACTGACTAC CCACTGACTT AGCTCCCTAT TTAAAGGCAC CTTACACTGA CGTAATGACC    34740
AAAGGTCTAA AAACCCCGCC AAAAAAACAC ACACGCCCTG GGTGTTTTTG CGAAAACACT    34800
TCCGCGTTCT CACTTCCTCG TATCGATTTC GTGACTTGAC TTCCGGGTTC CCACGTTACG    34860
TCACTTTTGC CCTTACATGT AACTTAGTCG TAGGGCGCCA TCTTGCCCAC GTCCAAAATG    34920
GCTTACATGT CCAGTTACGC CTCCGCGGCG ACCGTTAGCC GTGCGTCGTG ACGTCATTTG    34980
CATCAACGTT TCTCGGCCAA TCAGCAGTAG CCCCGCCCTA AATTTAAAAC CTCATTGCAT    35040
ATTAACTTTT GTTTACTTTG TGGGGTATAT TATTGATGAT G                       35081
```

(2) INFORMATION FOR SEQ ID NO:2:

(i) SEQUENCE CHARACTERISTICS:
  (A) LENGTH: 1101 base pairs
  (B) TYPE: nucleic acid
  (C) STRANDEDNESS: single
  (D) TOPOLOGY: linear (xi) SEQUENCE DESCRIPTION: SEQ ID NO:2:

```
ATGTCAAAGA GGCTCCGGGT GGAAGATGAC TTCAACCCCG TCTACCCCTA TGGCTACGCG      60
CGGAATCAGA ATATCCCCTT CCTCACTCCC CCCTTTGTCT CCTCCGATGG ATTCAAAAAC     120
TTCCCCCCTG GGGTCCTGTC ACTCAAACTG GCTGACCCAA TCACCATAGC CAATGGTGAT     180
GTCTCACTCA AGGTGGGAGG GGGACTTACT TTGCAAGAAG GAAGTCTGAC TGTAGACCCT     240
AAGGCTCCCT TGCAACTTGC AAACAATAAA AAACTTGAGC TTGTTTATGT TGATCCATTT     300
GAGGTTAGTG CCAATAAACT TAGTTTAAAA GTAGGACATG GATTAAAAAT ATTAGATGAC     360
AAAAGTGCTG GAGGGTTGAA AGATTTAATT GGCAAACTTG TGGTTTTAAC AGGGAAAGGA     420
ATAGGCACTG AAAATTTGCA AAATACAGAT GGTAGCAGCA GAGGAATTGG TATAAGTGTA     480
AGAGCAAGAG AAGGGTTAAC ATTTGACAAT GATGGATACT RGGTAGCATG GAACCCAAAG     540
TATGACACGC GCACACTTTG GACAACACCA GACACATCTC CTAATTGCAG GATTGATAAG     600
GAGAAGGATT CAAAACTCAC TTTGGTACTT ACAAAGTGTG GAAGTCAAAT ATTAGCTAAT     660
```

-continued

| | | | | | | |
|---|---|---|---|---|---|---|
| GTGTCTTTGA | TTGTGGTGTC | AGGAAAATAT | CAATACATAG | ACCACGCTAC | AAATCCAACT | 720 |
| CTTAAATCAT | TTAAATAAA | ACTTCTTTTT | GATAATAAAG | GTGTACTTCT | CCCAAGTTCA | 780 |
| AACCTTGATT | CCACATATTG | GAACTTTAGA | AGTGACAATT | TAACTGTATC | TGAGGCATAT | 840 |
| AAAAATGCAG | TTGAATTTAT | GCCTAATTTG | GTAGCCTACC | CAAAACCTAC | CACTGGCTCT | 900 |
| AAAAAATATG | CAAGGGATAT | AGTCTATGGG | AACATATATC | TTGGAGGTTT | GGCATATCAG | 960 |
| CCAGTTGTAA | TTAAGGTTAC | TTTTAATGAA | GAAGCAGATA | GTGCTTACTC | TATAACATTT | 1020 |
| GAATTTGTAT | GGAATAAAGA | ATATGCCAGG | GTTGAATTTG | AAACCACTTC | CTTTACCTTC | 1080 |
| TCCTATATTG | CCCAACAATA | A | | | | 1101 |

( 2 ) INFORMATION FOR SEQ ID NO:3:

( i ) SEQUENCE CHARACTERISTICS:
        ( A ) LENGTH: 1552 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | | |
|---|---|---|---|---|---|---|
| ATGAGGCGTG | CGGTGGTGTC | TTCCTCTCCT | CCTCCCTCGT | ACGAGAGCGT | GATGGCGCAG | 60 |
| GCGACCCTGG | AGGTTCCGTT | TGTGCCTCCG | CGGTATATGG | CTCCTACGGA | GGGCAGAAAC | 120 |
| AGCATTCGTT | ACTCGGAGCT | GGCTCCGTTG | TACGACACCA | CTCGCGTGTA | CTTGGTGACA | 180 |
| ACAAGTCGGC | GGACATCGCT | TCCCTGAACT | ATCAAAACGA | CCACAGCAAC | TTCCTGACCA | 240 |
| CGGTGGTGCA | GAACAACGAT | TTCACCCCCG | CCGAGGCTAG | CACGCAGACG | ATAAATTTTG | 300 |
| ACGAGCGGTC | GCGGTGGGGC | GGTGATCTGA | AGACCATTCT | GCACACCAAC | ATGCCCAATG | 360 |
| TGAACGAGTA | CATGTTCACC | AGCAAGTTTA | AGGCGCGGGT | GATGGTGGCT | AGAAAACACC | 420 |
| CACAGGGGGT | AGAAGCAACA | GATTTAAGCA | AGGATATCTT | AGAGTATGAG | TGGTTTGAGT | 480 |
| TTACCCTGCC | CGAGGGCAAC | TTTTCCGAGA | CCATGACCAT | AGACCTGATG | AACAACGCCA | 540 |
| TCTTGGAAAA | CTACTTGCAA | GTGGGGCGGC | AAAATGGCGT | GCTGGAGAGC | GATATTGGAG | 600 |
| TCAAGTTTGA | CAGCAGAAAT | TTCAAGCTGG | GCTGGGACCC | TGTGACCAAG | CTGGTGATGC | 660 |
| CAGGGGTCTA | CACCTACGAG | GCCTTTCACC | CGGACGTGGT | GCTGCTGCCG | GCTGCGGGG | 720 |
| TGGACTTCAC | AGAGAGCCGC | CTGAGCAACC | TCCTGGGCAT | TCGCAAGAAG | CAACCTTTCC | 780 |
| AAGAGGGCTT | CAGAATCATG | TATGAGGATC | TAGAAGGGGG | CAACATCCCC | GCCCTGCTGG | 840 |
| ATGTGCCCAA | GTACTTGGAA | AGCAAGAAGA | AGTTAGAGGA | GGCATTGGAG | AATGCTGCTA | 900 |
| AAGCTAATGG | TCCTGCAAGA | GGAGACAGTA | GCGTCTCAAG | AGAGGTTGAA | AAGGCAGCTG | 960 |
| AAAAAGAACT | TGTTATTGAG | CCCATCAAGC | AAGATGATAC | CAAGAGAAGT | TACAACCTCA | 1020 |
| TCGAGGGAAC | CATGGACACG | CTGTACCGCA | GCTGGTACCT | GTCCTATACC | TACCGGGACC | 1080 |
| CTGAGAACGG | GGTGCAGTCG | TGGACGCTGC | TCACCACCCC | GGACGTCACC | TGCGGCGCGG | 1140 |
| AGCAAGTCTA | CTGGTCGCTG | CCGGACCTCA | TGCAAGACCC | CGTCACCTTC | CGTTCTACCC | 1200 |
| AGCAAGTCAG | CAACTACCCC | GTGGTCGGCG | CCGAGCTCAT | GCCCTTCCGC | GCCAAGAGCT | 1260 |
| TTACAACGAC | CTCGCCGTCT | ACTCCCAGCT | CATCCGCAGC | TACACCTCCC | TCACCCACGT | 1320 |
| CTTCAACCGC | TTCCCCGACA | ACCAGATCCT | CTGCCGTCCG | CCCGCGCCCA | CCATCACCAC | 1380 |
| CGTCAGTGAA | AACGTGCCTG | CTCTCACAGA | TCACGGGACG | CTACCGCTGC | GCAGCAGTAT | 1440 |
| CCGCGGAGTC | CAGCGAGTGA | CCGTCACTGA | CGCCCGTCGC | CGCACCTGTC | CCTACGTCTA | 1500 |
| CAAGGCCCTG | GGCATAGTCG | CGCCGCGTGT | GCTTTCCAGT | CGCACCTTCT | AA | 1552 |